United States Patent
Komkova et al.

(10) Patent No.: US 11,554,361 B2
(45) Date of Patent: Jan. 17, 2023

(54) MIXED-MODE CHROMATOGRAPHY MEMBRANES

(71) Applicant: Merck Millipore Ltd., Carrigtwohill (IE)

(72) Inventors: Elena N. Komkova, Hamilton (CA); Charles H. Honeyman, Toronto (CA)

(73) Assignee: Merck Millipore Ltd., Carrigtwohill (IE)

( * ) Notice: Subject to any disclaimer, the term of this patent is extended or adjusted under 35 U.S.C. 154(b) by 0 days.

(21) Appl. No.: 16/055,786

(22) Filed: Aug. 6, 2018

(65) Prior Publication Data
US 2018/0353939 A1 Dec. 13, 2018

Related U.S. Application Data

(62) Division of application No. 14/190,650, filed on Feb. 26, 2014, now abandoned.
(Continued)

(51) Int. Cl.
  *B01D 15/32* (2006.01)
  *B01D 15/36* (2006.01)
(Continued)

(52) U.S. Cl.
  CPC ........ *B01J 20/3285* (2013.01); *B01D 15/327* (2013.01); *B01D 15/36* (2013.01);
(Continued)

(58) Field of Classification Search
  CPC .... B01D 67/0006; B01D 69/02; B01D 69/10; B01D 69/141; B01D 71/40; B01D 15/36;
(Continued)

(56) References Cited

U.S. PATENT DOCUMENTS 3,991,017 A  11/1976 Barrett et al.
5,629,084 A   5/1997 Moya
(Continued)

FOREIGN PATENT DOCUMENTS

EP  2 143 481 A1  1/2010
EP   2412433 A2   2/2012
(Continued)

OTHER PUBLICATIONS

Liu, H., et al., "Recovery and purification process development for monoclonal antibody production", mAbs, 2:5, pp. 480-499. (Year: 2010).*

(Continued)

*Primary Examiner* — Benjamin L Lebron
(74) *Attorney, Agent, or Firm* — Foley Hoag LLP

(57) ABSTRACT

Described are composite materials and methods of using them for mixed-mode chromatography. In certain embodiments, the composite material comprises a support member, comprising a plurality of pores extending through the support member; and a multi-functional cross-linked gel. The multi-functional cross-linked gel possesses at least two of the following functions or characteristics: cationic, anionic, hydrophobic, hydrophilic, thiophilic, hydrogen bond donating, hydrogen bond accepting, pi-pi bond donating, pi-pi bond accepting, or metal chelating. The composite materials may be used in the separation or purification of a biological molecule or biological ion.

19 Claims, 16 Drawing Sheets

Related U.S. Application Data

(60) Provisional application No. 61/769,330, filed on Feb. 26, 2013.

(51) Int. Cl.

| | | |
|---|---|---|
| *B01D 15/38* | (2006.01) | |
| *B01J 20/28* | (2006.01) | |
| *B01J 20/286* | (2006.01) | |
| *B01J 20/291* | (2006.01) | |
| *B01J 20/32* | (2006.01) | |
| *B01J 39/26* | (2006.01) | |
| *B01J 41/20* | (2006.01) | |
| *B01J 43/00* | (2006.01) | |
| *B01J 47/12* | (2017.01) | |
| *C07K 1/16* | (2006.01) | |

(52) U.S. Cl.
CPC ......... *B01D 15/362* (2013.01); *B01D 15/363* (2013.01); *B01D 15/3847* (2013.01); *B01J 20/286* (2013.01); *B01J 20/28033* (2013.01); *B01J 20/291* (2013.01); *B01J 39/26* (2013.01); *B01J 41/20* (2013.01); *B01J 43/00* (2013.01); *B01J 47/12* (2013.01); *C07K 1/165* (2013.01)

(58) Field of Classification Search
CPC ................ B01D 15/327; B01D 15/362; B01D 15/363; B01D 15/3847; B01J 20/265; B01J 20/267; B01J 20/28004; B01J 20/28011; B01J 20/28023; B01J 20/28033; B01J 20/38047; B01J 20/28069; B01J 20/28078; B01J 20/28085; B01J 20/28097; B01J 20/285; B01J 20/286; B01J 20/291; B01J 20/3282; B01J 43/00; B01J 20/3285; B01J 39/26; B01J 41/20; B01J 47/12; C07K 1/165
See application file for complete search history.

(56) References Cited

U.S. PATENT DOCUMENTS

| | | | |
|---|---|---|---|
| 5,647,979 A | 7/1997 | Liao et al. | |
| 5,814,372 A | 9/1998 | Moya | |
| 7,073,671 B2 | 7/2006 | Charkoudian | |
| 7,284,668 B2 | 10/2007 | Charkoudian | |
| 7,385,040 B2 | 6/2008 | Johansson et al. | |
| 7,714,112 B2 | 5/2010 | Engstrand et al. | |
| 7,750,129 B2 | 7/2010 | Johansson et al. | |
| 7,867,784 B2 | 1/2011 | Engstrand et al. | |
| 2004/0203149 A1 | 10/2004 | Childs et al. | |
| 2005/0211615 A1* | 9/2005 | DiLeo .................. | B01J 20/3293 210/198.2 |
| 2008/0264867 A1 | 10/2008 | Mika et al. | |
| 2009/0176052 A1 | 7/2009 | Childs et al. | |
| 2010/0059443 A1 | 3/2010 | Brellisford et al. | |
| 2010/0181254 A1 | 7/2010 | Graalfs | |
| 2010/0311850 A1 | 12/2010 | Wickert et al. | |
| 2011/0068002 A1 | 3/2011 | Lin et al. | |
| 2011/0117626 A1 | 5/2011 | Komkova et al. | |
| 2012/0052550 A1 | 3/2012 | Woonton et al. | |
| 2012/0064601 A1 | 3/2012 | Komkova et al. | |

FOREIGN PATENT DOCUMENTS

| | | |
|---|---|---|
| JP | S5147588 A | 4/1976 |
| JP | 2012032392 A | 2/2012 |
| WO | WO-96/03202 | 2/1996 |
| WO | WO-03/103814 | 12/2003 |
| WO | WO-2004/073843 A1 | 9/2004 |
| WO | WO-2005/120701 A1 | 12/2005 |
| WO | WO-2006/015495 | 2/2006 |
| WO | WO-2010/002502 A2 | 1/2010 |
| WO | WO-2010/031144 A1 | 3/2010 |
| WO | WO-2011/058439 A1 | 5/2011 |
| WO | WO-2011/146179 A2 | 11/2011 |
| WO | WO-2012/015379 A1 | 2/2012 |
| WO | WO-2014/134147 A1 | 9/2014 |

OTHER PUBLICATIONS

Follman et al., "Factorial screening of antibody purification processes using three chromatography steps without protein A," Journal of Chromatography A, 1024:79-85 (2004).

International Search Report dated Jun. 2, 2014, from PCT/US2014/018635.

Low et al., "Future of antibody purification," Journal of Chromatography B, 848:48-63 (2007).

Neidhardt et al., "Rapid, two-step purification process for the preparation of pyrogen-free murine immunoglobulin G1 monoclonal antibodies," Journal of Chromatography, 590:255-261 (1992).

Pezzini et al., "Antibody capture by mixed-mode chromatography: A comprehensive study from determination of optimal purification conditions to identification of contaminating host cell proteins," Journal of Chromatography A, 1218:8197-8208 (2011).

Supplementary European Search Report dated Sep. 21, 2016, from EP 14 75 6874.

Voitl et al., "Application of mixed mode resins for the purification of antibodies," Journal of Chromatography A, 1217:5753-5760 (2010).

Yang et al., "Mixed-mode chromatography and its applications to biopolymers," Journal of Chromatography A, 1218(49):8813-8825 (2011).

Greenley., "Free Radical Copolymerization Reactivity Ratios," Polymer Handbook Fourth Edition: 8 pages (1999).

Lee et al., "The kinetics of vinyl acrylate photopolymerization," Polymer, 44: 2859-2865 (2003).

Mukherjee et al., "Compositional and Stereochemical Analysis of Acrylamide/Vinyl Acetate Copolymers by One- and Two-Dimensional NMR Spectroscopy," Macromolecules, 31: 8455-8462 (1998).

Extended European Search Report for EP Application No. 22163387.8 dated Aug. 18, 2022.

* cited by examiner

| Cycle number | mAbs dynamic binding capacity (mg/mL) | % Aggregates in eluent B | % Mabs in eluent B | % Fragments in eluent B |
|---|---|---|---|---|
| 1 | 185.0 | 0.11 | 99.84 | 0.05 |
| 2 | 186.2 | 0.12 | 99.87 | 0.01 |
| 3 | 184.3 | 0.11 | 99.88 | 0.01 |

| Protein/mAbs | Toyopearl MX-Trp-650M (Tosoh Biosciences) | Capto MMC (GE Health care) | Mixed-mode membrane (Natrix) |
|---|---|---|---|
| Lysozyme | - | 55.0 | 135.0 |
| mAbs/IgG | 90.0 | - | 220.1 |

| Sample | % Peak area | | | Aggregates clearance (%) |
|---|---|---|---|---|
| | Aggregates (10.2 min) | mAbs monomers (12.5 min) | Fragments (17.6 min) | |
| Feed | 1.79 | 98.14 | 0.07 | - |
| Fraction A6 | 0 | 100 | 0 | 100 |
| Fraction A7 | 0 | 100 | 0 | 100 |
| Fraction A8 | 0.16 | 99.84 | 0 | 91.0 |

| Sample | HCP (ppm) | HCP clearance (%) | Absorbance $A_{260}/A_{280}$ | DNA (ng/mL) | DNA clearance (%) | Yield (%) |
|---|---|---|---|---|---|---|
| Feed | 3,720.00 | - | - | 7,740.00 | - | - |
| Fraction ΣA1-A5 | 360.00 | 90.3 | - | 83.00 | 98.9 | |
| Fraction ΣA6-A8 | 410.00 | 89.0 | - | 10.00 | 99.8 | > 90.0 |
| Flowthrough fraction | - | - | 1.81 | - | - | - |

Figure 23

| Membrane | Monomers and XL (mol%) | | | | Solvents Used (wt%) | | | | | |
|---|---|---|---|---|---|---|---|---|---|---|
| | AMPS | Hm | HEAAm | BIS | DMAc | DPM | DMM | PrCarb | Prdiol | water |
| M-PhAAm | 69.25 | 5.18 | 12.25 | 13.32 | 23.12 | 34.75 | 20.65 | 6.14 | 4.61 | 10.72 |
| M-BuAAm | 68.56 | 5.82 | 12.92 | 12.71 | 23.13 | 34.43 | 21.05 | 5.61 | 5.46 | 10.32 |

Figure 24

| Membrane | Buffer Flux (kg/m$^2$h) | BC (mg/mL) | Recovery (%) | Swelling (%) | Mean Pore Size (μm) | Bubble Pt. Pore Size (μm) |
|---|---|---|---|---|---|---|
| M-PhAAm | 2,090.00 | 112.3 | > 90 | 12.1 | 0.65 | 1.47 |
| M-BuAAm | 2,410.00 | 107.7 | > 90 | 12.4 | 0.54 | 1.57 |

Figure 25

| Membrane | Monomers and XL (mol%) | | | | Solvents Used (wt%) | | | | | |
|---|---|---|---|---|---|---|---|---|---|---|
| | AMPS | BuAAm | CM | BIS | DMAc | DPM | DMM | PrCarb | Prdiol | water |
| M-NIPAM | 67.98 | 6.57 | 11.29 | 14.16 | 23.69 | 34.60 | 20.76 | 5.77 | 4.66 | 10.52 |
| M-DMAAm | 65.24 | 6.09 | 15.75 | 12.92 | 23.03 | 34.28 | 20.83 | 5.76 | 5.60 | 10.51 |
| M-DAAm | 68.44 | 5.84 | 10.46 | 15.27 | 23.12 | 34.39 | 20.37 | 6.30 | 5.20 | 10.63 |
| M-HEAAm | 68.56 | 5.82 | 12.92 | 12.71 | 23.13 | 34.43 | 21.05 | 5.61 | 5.46 | 10.32 |

Figure 26

| Membrane | Buffer Flux (kg/m$^2$h) | BC (mg/mL) | Recovery (%) | Swelling (%) | Mean Pore Size (μm) | | Bubble Pt. Pore Size (μm) | |
|---|---|---|---|---|---|---|---|---|
| | | | | | 4 min | 10 min | 4 min | 10 min |
| M-NIPAM | 2,870.00 | 104.1 | > 90 | 10.5 | 0.52 | 0.47 | 1.46 | 1.38 |
| M-DMAAm | 2,390.00 | 112.1 | > 90 | 11.9 | 0.61 | 0.54 | 1.70 | 1.25 |
| M-DAAm | 2,770.00 | 110.1 | > 90 | 11.7 | 0.50 | 0.55 | 1.40 | 1.52 |
| M-HEAAm | 2,410.00 | 107.7 | > 90 | 12.4 | 0.53 | 0.54 | 1.46 | 1.57 |

MIXED-MODE CHROMATOGRAPHY MEMBRANES

RELATED APPLICATIONS

This application is a divisional application of U.S. patent application Ser. No. 14/190,650, filed on Feb. 26, 2014; which claims the benefit of priority to U.S. Provisional Patent Application Ser. No. 61/769,330, filed on Feb. 26, 2013.

BACKGROUND OF THE INVENTION

Mixed-mode chromatography (MMC), also known as multimodal chromatography, refers to chromatographic method for separating one analyte from another by utilizing more than one form of interaction between the stationary phase and analytes. Importantly, the secondary interactions in MMC must be strong enough to contribute to retention of the analyte; this approach is distinct from conventional single-mode chromatography.

MMC has many advantages over traditional single-mode chromatography, and over other methods of separation. MMC exhibits higher selectivity than single-mode chromatography. For example, positive, negative and neutral substances could be separated by a reversed phase (RP)/anion-cation exchange (ACE) column in a single run. In addition, mixed-mode chromatographic media display a remarkably higher loading capacity. Because MMC uses two forms of interaction, one mixed-mode column can replace two or even more single mode columns; so, MMC is economical and reduces waste.

The ability to combine and streamline separation methods can enhance selectivity in a protein purification process. Unlike affinity chromatography, where a known site on the protein is targeted, mixed-mode ligands are not tailored to a known specific site. Accordingly, screening mixed-mode media becomes a search for sites on the target protein that provide useful affinity and selectivity.

Monoclonal antibodies constitute the largest number of protein-based therapeutic molecules in current use or in clinical trials. Protein A chromatography is routinely employed as a first capture step in industrial monoclonal antibody purification processes due to its high selectivity, resulting in good overall yields and purities. However, a major drawback of affinity chromatography is its high price, which, especially in case of therapeutic antibodies needed at high doses or for chronic administration, can account for a significant component of the cost of goods. In addition, leached protein A ligand from the affinity matrix must be removed by further chromatography steps due to its potential immunogenicity (Roque A. C. et al. Biotechnology Progress 20(2004), 639-654). In addition, traditional protein A chromatography requires elution at low pH, which can result in product aggregation or precipitation.

Monoclonal antibodies can be separated by MMC on multimodal media exhibiting, for instance, ionic and hydrophobic functionalities. These multimodal media offer a valuable alternative to the classical affinity approach for the separation of monoclonal antibodies. Due to the salt tolerability of the hydrophobic component, the clarified cell culture supernatant can be directly loaded on the matrix, resulting in an effective capturing of the monoclonal antibody. However, due to the multimodal nature of the resin, different types of interaction of the ligand with a particular monoclonal antibody are possible, requiring unique wash and elution conditions, differing from traditional ion-exchange or hydrophobic interaction chromatography.

There exists a need for MMC media and methods that display enhanced selectivity, high flow velocity, and low back pressure, are inexpensive, and allow for longer column lifetimes, reduced process times, increased productivity, and operational flexibility compared to affinity based methods.

BRIEF SUMMARY OF THE INVENTION

In certain embodiments, the invention relates to a composite material, comprising:
a support member, comprising a plurality of pores extending through the support member; and
a cross-linked gel, wherein the cross-linked gel comprises a first functionality and a second functionality; the first functionality and the second functionality are cationic, anionic, hydrophobic, hydrophilic, thiophilic, hydrogen bond donating, hydrogen bond accepting, pi-pi bond donating, pi-pi bond accepting, or metal chelating; and the first functionality is different from the second functionality,
wherein the cross-linked gel is located in the pores of the support member.

In certain embodiments, the invention relates to a composite material, comprising:
a support member, comprising a plurality of pores extending through the support member; and
a cross-linked gel, wherein the cross-linked gel comprises a first functionality and a second functionality; the first functionality and the second functionality are strong cations, weak cations, strong anions, weak anions, hydrophobic, hydrophilic, thiophilic, hydrogen bond donating, hydrogen bond accepting, pi-pi bond donating, pi-pi bond accepting, or metal chelating; and the first functionality is different from the second functionality;
wherein the cross-linked gel is located in the pores of the support member.

In certain embodiments, the invention relates to a method, comprising the step of:
contacting at a first flow rate a first fluid comprising a substance with any one of the aforementioned composite materials, thereby adsorbing or absorbing a portion of the substance onto the composite material.

In certain embodiments, the invention relates to a method, comprising the step of:
contacting at a first flow rate a first fluid comprising a substance and an unwanted material with any one of the aforementioned composite materials, thereby adsorbing or absorbing a portion of the unwanted material onto the composite material.

In certain embodiments, the invention relates to a method of making a composite material, comprising the steps of:
combining a first monomer, a photoinitiator, a cross-linking agent, and a solvent, thereby forming a monomeric mixture;
contacting a support member with the monomeric mixture, thereby forming a modified support member; wherein the support member comprises a plurality of pores extending through the support member, and the average pore diameter of the pores is about 0.1 to about 25 µm;
covering the modified support member with a polymeric sheet, thereby forming a covered support member; and irradiating the covered support member for a period of time, thereby forming a composite material.

BRIEF DESCRIPTION OF THE FIGURES

FIG. 23 tabulates formulation components and concentrations used to make mixed-mode strong cation-exchange membranes.

FIG. 24 tabulates performance characteristics of mixed-mode strong cation-exchange membranes.

FIG. 25 tabulates formulation components and concentrations used to make mixed-mode strong cation-exchange membranes.

FIG. 26 tabulates performance characteristics mixed-mode strong cation-exchange membranes.

DETAILED DESCRIPTION OF THE INVENTION

Overview

Figure 1:
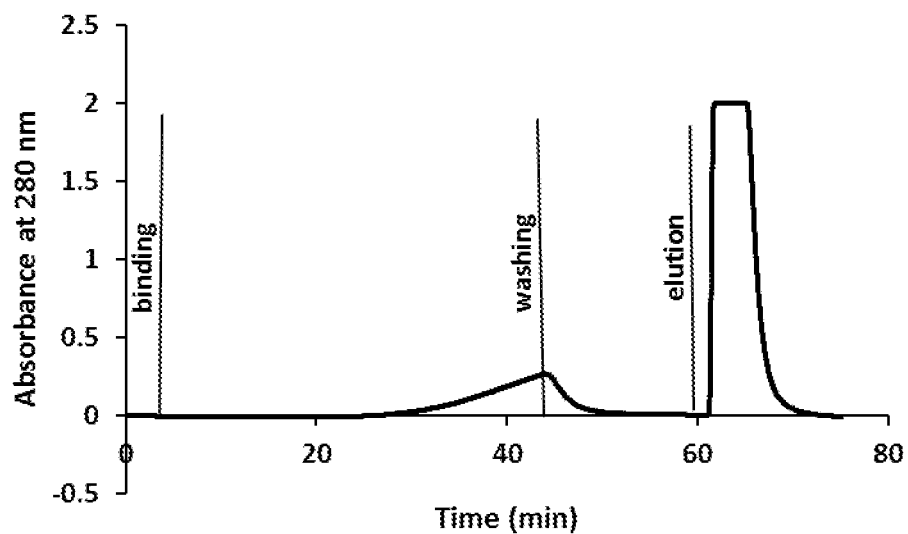
FIG. 1 depicts the performance of a mixed-mode membrane in a hIgG bind-elute experiment.

In certain embodiments, the invention relates to the preparation and use of membrane-based stationary phase mixed-mode chromatographic supports that employ multiple chemical mechanisms to adsorb or separate proteins or other solutes. In certain embodiments, the invention relates to purification of a protein from a mixture containing other materials, including fragmented or aggregated antibodies, host cell proteins, DNA, endotoxins, and viruses. Examples include, but are not limited to, chromatographic supports that exploit combination of at least two or possibly more of the following mechanisms: cation exchange, anion exchange, hydrophobic interaction, hydrophilic interaction, thiophilic interaction, hydrogen bonding, pi-pi bonding, and metal affinity.

In certain embodiments, the composite materials of the invention can be effectively used in both "bind-elute" and "flow-through" modes. Importantly, since the individual functionalities are included through the incorporation of functional monomers, the relative amount of each functional group can be easily and readily tuned for optimal performance characteristics.

"Bind-elute mode" as it relates to invention herein, refers to an operational approach to chromatography in which the buffer conditions are established so that both a target protein and undesired contaminants bind to the mixed mode chromatographic support or composite material. Fractionation of target protein from the other components is achieved subsequently by changing the conditions such that the target protein and contaminants are eluted separately from the support. In certain embodiments, a multimodal cation-exchange membrane of the invention may be used in "bind-elute mode" featuring high dynamic binding capacities at high conductivity, high volume throughput and selectivity. In certain embodiments, the eluent is reduced in aggregates of the target protein by about 50% to about 99%. In certain embodiments, the eluent is reduced in aggregates of the target protein by about 90%, about 91%, about 92%, about 93%, about 94%, about 95%, about 96%, about 97%, about 98%, or about 99%.

As it relates to the invention herein, the term "flow-through mode" refers to an operational approach to chromatography in which the buffer conditions are established so that the intact target protein flows through the membrane upon application while contaminants are selectively retained. In certain embodiments, a multimodal anion-exchange membrane of the invention may be used in "flow-through mode" in a post-protein A purification process to remove key contaminants such as DNA, host cell proteins (HCP), leached protein A, aggregates and viruses in a single step.

Various Characteristics of Exemplary Composite Materials

Composition of the Gels

In certain embodiments, the cross-linked gels may be formed through the in situ reaction of one or more polymerizable monomers with one or more cross-linkers. In certain embodiments, the gels may be formed through the reaction of one or more cross-linkable polymers with one or more cross-linkers. In certain embodiments, a cross-linked gel having macropores of a suitable size may be formed.

The gel can be selected to comprise specific monomers having specific functionality. Copolymers of these monomers can be used.

In certain embodiments, the properties of the composite materials may be tuned by adjusting the average pore diameter of the macroporous gel. The size of the macropores is generally dependent on the nature and concentration of the cross-linking agent, the nature of the solvent or solvents in which the gel is formed, the amount of any polymerization initiator or catalyst and, if present, the nature and concentration of porogen. In certain embodiments, the composite material may have a narrow pore-size distribution.

Porous Support Member

In some embodiments, the porous support member contains pores of average diameter between about 0.1 and about 25 μm.

In some embodiments, the porous support member has a volume porosity between about 40% and about 90%.

In certain embodiments, the porous support is flat.

In certain embodiments, the porous support is disk-shaped.

Many porous substrates or membranes can be used as the support member. In some embodiments, the porous support member is made of polymeric material. In certain embodiments, the support may be a polyolefin, which is available at low cost. In certain embodiments, the polyolefin may be poly(ethylene), poly(propylene), or poly(vinylidene difluoride). Extended polyolefin membranes made by thermally induced phase separation (TIPS), or non-solvent induced phase separation are mentioned. In certain embodiments, the support member may be made from natural polymers, such as cellulose or its derivatives. In certain embodiments, suitable supports include polyethersulfone membranes, poly(tetrafluoroethylene) membranes, nylon membranes, cellulose ester membranes, fiberglass, or filter papers.

In certain embodiments, the porous support is composed of woven or non-woven fibrous material, for example, a polyolefin such as polypropylene. Such fibrous woven or non-woven support members can have pore sizes larger than the TIPS support members, in some instances up to about 75 μm. The larger pores in the support member permit formation of composite materials having larger macropores in the macroporous gel. Non-polymeric support members can also be used, such as ceramic-based supports. The porous support member can take various shapes and sizes.

In some embodiments, the support member is in the form of a membrane.

In some embodiments, the support member has a thickness from about 10 to about 2000 μm, from about 10 to about 1000 μm, or from about 10 to about 500 μm.

In other embodiments, multiple porous support units can be combined, for example, by stacking. In one embodiment, a stack of porous support membranes, for example, from 2 to 10 membranes, can be assembled before the gel is formed within the void of the porous support. In another embodiment, single support member units are used to form composite material membranes, which are then stacked before use.

Relationship Between Gel and Support Member

The gel may be anchored within the support member. The term "anchored" is intended to mean that the gel is held within the pores of the support member, but the term is not necessarily restricted to mean that the gel is chemically bound to the pores of the support member. The gel can be held by the physical constraint imposed upon it by enmeshing and intertwining with structural elements of the support member, without actually being chemically grafted to the support member, although in some embodiments, the gel may be grafted to the surface of the pores of the support member.

Because the macropores are present in the gel that occupies the pores of the support member, the macropores of the gel must be smaller than the pores of the support member. Consequently, the flow characteristics and separation characteristics of the composite material are dependent on the characteristics of the gel, but are largely independent of the characteristics of the porous support member, with the proviso that the size of the pores present in the support member is greater than the size of the macropores of the gel. The porosity of the composite material can be tailored by filling the support member with a gel whose porosity is partially or completely dictated by the nature and amounts of monomer or polymer, cross-linking agent, reaction solvent, and porogen, if used. As pores of the support member are filled with the same gel material, a high degree of consistency is achieved in properties of the composite material, and for a particular support member these properties are determined partially, if not entirely, by the properties of the gel. The net result is that the invention provides control over macropore-size, permeability and surface area of the composite materials.

The number of macropores in the composite material is not primarily dictated by the number of pores in the support material. The number of macropores in the composite material can be much greater than the number of pores in the support member because the macropores are smaller than the pores in the support member. As mentioned above, the effect of the pore-size of the support material on the pore-size of the macroporous gel is generally negligible. An exception is found in those cases where the support member has a large difference in pore-size and pore-size distribution, and where a macroporous gel having very small pore-sizes and a narrow range in pore-size distribution is sought. In these cases, large variations in the pore-size distribution of the support member are weakly reflected in the pore-size distribution of the macroporous gel. In certain embodiments, a support member with a narrow pore-size range may be used in these situations.

In certain embodiments, the invention relates to any one of the aforementioned composite materials, wherein the composite materials are relatively non-toxic.

In certain embodiments, the invention relates to any one of the aforementioned composite materials, wherein the composite materials are tolerant to relatively wide ranges of salt concentration in the contacting liquid.

Preparation of Composite Materials

In certain embodiments, the composite materials of the invention may be prepared by single-step methods. In certain embodiments, these methods may use water or other environmentally benign solvents as the reaction solvent. In certain embodiments, the methods may be rapid and, therefore, may lead to relatively simple and low-cost manufacturing processes.

In certain embodiments, the composite materials of the invention may be prepared by mixing more than one monomer, one or more cross-linking agents, one or more initiators, and optionally one or more porogens, in one or more suitable solvents. In certain embodiments, the resulting mixture may be homogeneous. In certain embodiments, the mixture may be heterogeneous. In certain embodiments, the mixture may then be introduced into a suitable porous support, where a gel forming reaction may take place.

In certain embodiments, suitable solvents for the gel-forming reaction include 1,3-butanediol, di(propylene glycol) propyl ether, N,N-dimethylacetamide, di(propylene glycol) dimethyl ether, 1,2-propanediol, di(propylene glycol) methyl ether acetate (DPMA), water, dioxane, dimethylsulfoxide (DMSO), dimethylformamide (DMF), acetone, ethanol, N-methylpyrrolidone (NMP), tetrahydrofuran (THF), ethyl acetate, acetonitrile, N-methylacetamide, propanol, methanol, tri(ethylene glycol) dimethyl ether, tri (propylene glycol) butyl ether, tri(propylene glycol) propyl ether, or mixtures thereof. In certain embodiments, solvents that have a higher boiling point may be used, as these solvents reduce flammability and facilitate manufacture. In certain embodiments, solvents that have a low toxicity may be used, so they may be readily disposed of after use. An example of such a solvent is dipropyleneglycol monomethyl ether (DPM).

In certain embodiments, a porogen may be added to the reactant mixture, wherein porogens may be broadly described as pore-generating additives. In certain embodiments, the porogen may be selected from the group consisting of thermodynamically poor solvents and extractable polymers, for example, poly(ethyleneglycol), surfactants, and salts.

In some embodiments, components of the gel forming reaction react spontaneously at room temperature to form the gel. In other embodiments, the gel forming reaction must be initiated. In certain embodiments, the gel forming reaction may be initiated by any known method, for example, through thermal activation or UV radiation. In certain embodiments, the reaction may be initiated by UV radiation in the presence of a photoinitiator. In certain embodiments, the photoinitiator may be selected from the group consisting of 2-hydroxy-1-[4-2(hydroxyethoxy)phenyl]-2-methyl-1-propanone (Irgacure 2959), 2,2-dimethoxy-2-phenylacetophenone (DMPA), benzophenone, benzoin and benzoin ethers, such as benzoin ethyl ether and benzoin methyl ether, dialkoxyacetophenones, hydroxyalkylphenones, and α-hydroxymethyl benzoin sulfonic esters. Thermal activation may require the addition of a thermal initiator. In certain embodiments, the thermal initiator may be selected from the group consisting of 1,1'-azobis(cyclohexanecarbonitrile) (VAZO® catalyst 88), azobis(isobutyronitrile) (AIBN), potassium persulfate, ammonium persulfate, and benzoyl peroxide.

In certain embodiments, the gel-forming reaction may be initiated by UV radiation. In certain embodiments, a photoinitiator may be added to the reactants of the gel forming reaction, and the support member containing the mixture of monomer, cross-linking agent, and photoinitiator may be exposed to UV radiation at wavelengths from about 250 nm to about 400 nm for a period of a few seconds to a few hours. In certain embodiments, the support member containing the mixture of monomer, cross-linking agent, and photoinitiator may be exposed to UV radiation at about 350 nm for a period of a few seconds to a few hours. In certain embodiments, the support member containing the mixture of monomer, cross-linking agent, and photoinitiator may be exposed to UV radiation at about 350 nm for about 10 minutes. In certain embodiments, visible wavelength light may be used to initiate the polymerization. In certain embodiments, the support member must have a low absorbance at the wavelength used so that the energy may be transmitted through the support member.

In certain embodiments, the rate at which polymerization is carried out may have an effect on the size of the macropores obtained in the macroporous gel. In certain embodiments, when the concentration of cross-linker in a gel is increased to sufficient concentration, the constituents of the gel begin to aggregate to produce regions of high polymer density and regions with little or no polymer, which latter regions are referred to as "macropores" in the present specification. This mechanism is affected by the rate of polymerization. In certain embodiments, the polymerization may be carried out slowly, such as when a low light intensity in the photopolymerization is used. In this instance, the aggregation of the gel constituents has more time to take place, which leads to larger pores in the gel. In certain embodiments, the polymerization may be carried out at a high rate, such as when a high intensity light source is used. In this instance, there may be less time available for aggregation and smaller pores are produced.

In certain embodiments, once the composite materials are prepared, they may be washed with various solvents to remove any unreacted components and any polymer or oligomers that are not anchored within the support. In certain embodiments, solvents suitable for the washing of the composite material include water, acetone, methanol, ethanol, propanol, and DMF.

Exemplary Uses of the Composite Materials

In certain embodiments, the invention relates to a method, wherein a fluid is passed through the cross-linked gel of any one of the aforementioned composite materials. By tailoring the conditions for binding or fractionation, good selectivity can be obtained.

In certain embodiments, the invention relates to a method of separating biomolecules, such as proteins or immunoglobulins, from solution. In certain embodiments, the invention relates to a method of purifying biomolecules such as proteins or immunoglobulins. In certain embodiments, the invention relates to a method of purifying proteins or monoclonal antibodies with high selectivity. In certain embodiments, the invention relates to a method, wherein the biological molecule or biological ion retains its tertiary or quaternary structure, which may be important in retaining biological activity. In certain embodiments, biological molecules or biological ions that may be separated or purified include proteins such as albumins, e.g., bovine serum albumin, and lysozyme. In certain embodiments, biological molecules or biological ions that may be separated include γ-globulins of human and animal origins, immunoglobulins such as IgG, IgM, or IgE of human and animal origins, proteins of recombinant and natural origin including protein A, phytochrome, halophilic protease, poly(3-hydroxybutyrate) depolymerase, aculaecin-A acylase, polypeptides of synthetic and natural origin, interleukin-2 and its receptor, enzymes such as phosphatase, dehydrogenase, ribonuclease A, etc., monoclonal antibodies, fragments of antibodies, trypsin and its inhibitor, albumins of varying origins, e.g., α-lactalbumin, human serum albumin, chicken egg albumin, ovalbumin etc., cytochrome C, immunoglobulins, myoglobulin, recombinant human interleukin, recombinant fusion protein, nucleic acid derived products, DNA and RNA of synthetic and natural origin, DNA plasmids, lectin, α-chymotrypsinogen, and natural products including small molecules. In certain embodiments, the invention relates to a method of recovering an antibody fragment from variants, impurities, or contaminants associated therewith. In certain embodiments, biomolecule separation or purification may occur substantially in the cross-linked gel. In certain embodiments, biomolecule separation or purification may occur substantially in the macropores of the macroporous cross-linked gel.

In certain embodiments, the invention relates to a method of reversible adsorption of a substance. In certain embodiments, an adsorbed substance may be released by changing the liquid that flows through the gel. In certain embodiments, the uptake and release of substances may be controlled by variations in the composition of the cross-linked gel.

In certain embodiments, the invention relates to a method, wherein the substance may be applied to the composite material from a buffered solution.

In certain embodiments, the invention relates to a method, wherein the substance may be eluted using varying concentrations of aqueous salt solutions.

In certain embodiments, the invention relates to a method that exhibits high binding capacities. In certain embodiments, the invention relates to a method that exhibits binding capacities of about 100 mg/mL$_{membrane}$, about 110 mg/mL$_{membrane}$, mg/about 120 mg/mL$_{membrane}$, about 130 mg/mL$_{membrane}$, about 140 mg/mL$_{membrane}$, about 150 mg/mL$_{membrane}$, about 160 mg/mL$_{membrane}$, about 170 mg/mL$_{membrane}$, about 180 mg/mL$_{membrane}$, about 190 mg/mL$_{membrane}$, about 200 mg/mL$_{membrane}$, about 210 mg/mL$_{membrane}$, about 220 mg/mL$_{membrane}$, about 230 mg/mL$_{membrane}$, about 240 mg/mL$_{membrane}$, about 250 mg/mL$_{membrane}$, about 260 mg/mL$_{membrane}$, about 270 mg/mL$_{membrane}$, about 280 mg/mL$_{membrane}$, about 290 mg/mL$_{membrane}$, about 300 mg/mL$_{membrane}$, about 310 mg/mL$_{membrane}$, about 320 mg/mL$_{membrane}$, about 330 mg/mL$_{membrane}$, about 340 mg/mL$_{membrane}$, about 350 mg/mL$_{membrane}$, about 360 mg/mL$_{membrane}$, about 370 mg/mL$_{membrane}$, about 380 mg/mL$_{membrane}$, about 390 mg/mL$_{membrane}$, or about 400 mg/mL$_{membrane}$ at 10% breakthrough.

In certain embodiments, methods of the invention result in binding capacities higher than those reported with the use of conventional MMC resins. In certain embodiments, the inventive methods may be run at significantly higher flow rates, due to convective flow, than the flow rates achieved in methods MMC resins. In certain embodiments, the methods of the present invention do not suffer from the problematic pressure drops associated with methods using MMC resins.

In certain embodiments, the flow rate during binding (the first flow rate) may be about 0.1 to about 10 mL/min. In certain embodiments, the flow rate during elution (the second flow rate) may be about 0.1 to about 10 mL/min. In certain embodiments, the first flow rate or the second flow rate may be about 0.1 mL/min, about 0.5 mL/min, about 1.0 mL/min, about 1.5 mL/min, about 2.0 mL/min, about 2.5 mL/min, about 3.0 mL/min, about 4.0 mL/min, about 4.5 mL/min, about 5.0 mL/min, about 5.5 mL/min, about 6.0 mL/min, about 6.5 mL/min, about 7.0 mL/min, about 7.5 mL/min, about 8.0 mL/min, about 8.5 mL/min, about 9.0 mL/min, about 9.5 mL/min, or about 10.0 mL/min. In certain embodiments, the first flow rate or the second flow rate may be about 0.5 mL/min to about 5.0 mL/min.

The water flux, $Q_{H2O}$ (kg/m²h), was calculated using the following equation:

$$Q_{H_2O} = \frac{(m_1 - m_2)}{A \cdot t}$$

where $m_1$ is the mass of water transferred through the membrane at $t_1$, $m_2$ is the mass of water transferred through the membrane at $t_2$, A is the membrane cross-sectional area and t is the elapsed time ($t_1-t_2$), where $t_1 > t_2$.

In certain embodiments, an additive may be added to the eluting salt solution (the second fluid, or the third or later fluid). In certain embodiments, the additive is added in a low concentration (e.g., less than about 1 M, about 0.5 M, or about 0.2 M). In certain embodiments, the additive is a water-miscible alcohol, a detergent, dimethyl sulfoxide, dimethyl formamide, or an aqueous solution of a chaotropic salt. In certain embodiments, not wishing to be bound by any particular theory, the additive may decrease the surface tension of water, thus weakening the hydrophobic interactions to give a subsequent dissociation of the ligand-solute complex.

In certain embodiments, the mixed-mode media combines both hydrophobic and ion-exchange characteristics, so that its selectivity can be manipulated in order for the retention magnitude of each retention mode may be adjusted by changing the mobile phase ionic strength, pH, or organic solvent content. In certain embodiments, the selectivity can be manipulated either concurrently or individually.

In certain embodiments, changing pH is an effective elution tool for protein elution without changing the conductivity of the mobile phase.

In certain embodiments, the invention relates to a one-step method of biomolecule purification. In certain embodiments, the invention relates to a method of biomolecule separation that is easier to scale-up, is less labor intensive, is faster, and has lower capital costs than the commonly used conventional packed-column chromatography techniques.

Pore Size Determination

SEM and ESEM

The average diameter of the macropores in the macroporous cross-linked gel may be estimated by any one of many methods. One method that may be employed is scanning electron microscopy (SEM). SEM is a well-established method for determining pore sizes and porosities in general, and for characterizing membranes in particular. Reference is made to the book Basic Principles of Membrane Technology by Marcel Mulder (© 1996) ("Mulder"), especially Chapter IV. Mulder provides an overview of methods for characterizing membranes. For porous membranes, the first method mentioned is electron microscopy. SEM is a very simple and useful technique for characterising microfiltration membranes. A clear and concise picture of the membrane can be obtained in terms of the top layer, cross-section and bottom layer. In addition, the porosity and pore size distribution can be estimated from the photographs.

Environmental SEM (ESEM) is a technique that allows for the non-destructive imaging of specimens that are wet, by allowing for a gaseous environment in the specimen chamber. The environmental secondary detector (ESD) requires a gas background to function and operates at from about 3 torr to about 20 torr. These pressure restraints limit the ability to vary humidity in the sample chamber. For example, at 10 torr, the relative humidity at a specific temperature is as follows:

| Relative Humidity at 10 torr (%) | T (° C.) |
| --- | --- |
| About 80 | About 16 |
| About 70 | About 18 |
| About 60 | About 20 |
| About 40 | About 24 |
| About 20 | About 40 |
| About 10 | About 50 |
| About 2 | About 70 |
| About 1 | About 100 |

This is a useful guide to relative humidity in the sample chamber at different temperatures. In certain embodiments, the relative humidity in the sample chamber during imaging is from about 1% to about 99%. In certain embodiments, the relative humidity in the sample chamber during imaging is about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%. In certain embodiments, the relative humidity in the sample chamber during imaging is about 45%.

In certain embodiments, the microscope has nanometer resolution and up to about 100,000× magnification.

In certain embodiments, the temperature in the sample chamber during imaging is from about 4° C. to about 95° C. In certain embodiments, the temperature in the sample chamber during imaging is about 4° C., about 6° C., about 8° C., about 10° C., about 12° C., about 14° C., about 16° C., about 18° C., about 20° C., about 25° C., about 30° C., about 35° C., about 40° C., about 45° C., about 50° C., about 55° C., about 60° C., about 65° C., about 70° C., about 75° C., about 80° C., or about 85° C. In certain embodiments, the temperature in the sample chamber during imaging is about 5° C.

In certain embodiments, the pressure in the sample chamber during imaging is from about 3 torr to about 20 torr. In certain embodiments, the pressure in the sample chamber during imaging is about 4 torr, about 6 torr, about 8 torr, about 10 torr, about 12 torr, about 14 torr, about 16 torr, about 18 torr, or about 20 torr. In certain embodiments, the pressure in the sample chamber during imaging is about 3 torr.

In certain embodiments, the working distance from the source of the electron beam to the sample is from about 6 mm to about 15 mm. In certain embodiments, the working distance from the source of the electron beam to the sample is about 6 mm, about 7 mm, about 8 mm, about 9 mm, about 10 mm, about 11 mm, about 12 mm, about 13 mm, about 14 mm, or about 15 mm. In certain embodiments, the working distance from the source of the electron beam to the sample is about 10 mm.

In certain embodiments, the voltage is from about 1 kV to about 30 kV. In certain embodiments, the voltage is about 2 kV, about 4 kV, about 6 kV, about 8 kV, about 10 kV, about 12 kV, about 14 kV, about 16 kV, about 18 kV, about 20 kV, about 22 kV, about 24 kV, about 26 kV, about 28 kV, or about 30 kV. In certain embodiments, the voltage is about 20 kV.

In certain embodiments, the average pore diameter may be measured by estimating the pore diameters in a representative sample of images from the top or bottom of a composite material. One of ordinary skill in the art will recognize and acknowledge various experimental variables associated with obtaining an ESEM image of a wetted membrane, and will be able to design an experiment accordingly.

Capillary Flow Porometry

Capillary flow porometry is an analytical technique used to measure the pore size(s) of porous materials. In this analytical technique, a wetting liquid is used to fill the pores of a test sample and the pressure of a non-reacting gas is used to displace the liquid from the pores. The gas pressure and flow rate through the sample is accurately measured and the pore diameters are determined using the following equation:

$$D = 4 \times \gamma \times \cos\theta / P$$

D = pore diameter
$\gamma$ = liquid surface tension
$\theta$ = liquid contact angle
P = differential gas pressure This equation shows that the pressure required to displace liquid from the wetted sample is inversely related to the pore size. Since this technique involves the flow of a liquid from the pores of the test sample under pressure, it is useful for the characterization of through pores (interconnected pores that allow fluid flow from one side of the sample to the other). Other pore types (closed and blind pores) are not detectable by this method.

Capillary flow porometry detects the presence of a pore when gas starts flowing through that pore. This occurs only when the gas pressure is high enough to displace the liquid from the most constricted part of the pore. Therefore, the pore diameter calculated using this method is the diameter of the pore at the most constricted part and each pore is detected as a single pore of this constricted diameter. The largest pore diameter (called the bubble point) is determined by the lowest gas pressure needed to initiate flow through a wet sample and a mean pore diameter is calculated from the mean flow pressure. In addition, both the constricted pore diameter range and pore size distribution may be determined using this technique.

This method may be performed on small membrane samples (2.5 cm diameter) that are immersed in a test fluid (e.g. water, buffer, alcohol). The range of gas pressure applied can be selected from 0 to 500 psi.

Other Methods of Determining Pore Diameter

Mulder describes other methods of characterizing the average pore size of a porous membrane, including atomic force microscopy (AFM) (page 164), permeability calculations (page 169), gas adsorption-desorption (page 173), thermoporometry (page 176), permporometry (page 179), and liquid displacement (page 181). The teachings of Mulder, and the references cited therein, form part of the common general knowledge in the field, and are hereby incorporated by reference.

Exemplary Composite Materials

In certain embodiments, the invention relates to a composite material, comprising:
  a support member, comprising a plurality of pores extending through the support member; and
  a cross-linked gel, wherein the cross-linked gel comprises a first functionality and a second functionality; the first functionality and the second functionality are cationic, anionic, hydrophobic, hydrophilic, thiophilic, hydrogen bond donating, hydrogen bond accepting, pi-pi bond donating, pi-pi bond accepting, or metal chelating; and the first functionality is different from the second functionality,
  wherein the cross-linked gel is located in the pores of the support member.

In certain embodiments, the invention relates to a composite material, comprising:
  a support member, comprising a plurality of pores extending through the support member; and
  a cross-linked gel, wherein the cross-linked gel comprises a first functionality and a second functionality; the first functionality and the second functionality are strong cations, weak cations, strong anions, weak anions, hydrophobic, hydrophilic, thiophilic, hydrogen bond donating, hydrogen bond accepting, pi-pi bond donating, pi-pi bond accepting, or metal chelating; and the first functionality is different from the second functionality;
  wherein the cross-linked gel is located in the pores of the support member.

In certain embodiments, the invention relates to any one of the aforementioned composite materials, wherein the first functionality is a strong cation; and the second functionality is a weak cation.

In certain embodiments, the invention relates to any one of the aforementioned composite materials, wherein more than two functionalities are employed. In certain embodiments, the invention relates to any one of the aforementioned composite materials, wherein three, four, five, six, seven, eight, or nine different functionalities are employed.

In certain embodiments, the invention relates to any one of the aforementioned composite materials, wherein the first functionality or the second functionality is cationic. In certain embodiments, the cationic functionality is a weak cation. In certain embodiments, the cationic functionality is a strong cation. In certain embodiments, the strong cation is an ammonium cation. In certain embodiments, the first functionality or the second functionality is a trialkylammonium radical. In certain embodiments, the strong cation is a trimethylammonium radical. In certain embodiments, the weak cation is cationic only at a certain pH. In certain embodiments, the weak cation is a protonated ammonium radical. In certain embodiments, the weak cation is a protonated diialkylammonium radical. In certain embodiments, the weak cation is a protonated dimethylammonium radical.

In certain embodiments, the invention relates to any one of the aforementioned composite materials, wherein the first functionality or the second functionality is anionic. In certain embodiments, the anionic functionality is a weak anion. In certain embodiments, the cationic functionality is a strong anion. In certain embodiments, the strong anion is a sulfonate anion. In certain embodiments, the first functionality or the second functionality is a sulfonate radical. In certain embodiments, the first functionality or the second functionality is a sulfonate radical.

In certain embodiments, the invention relates to any one of the aforementioned composite materials, wherein the cross-linked gel is macroporous.

In certain embodiments, the invention relates to any one of the aforementioned composite materials, wherein the cationic, anionic, hydrophobic, hydrophilic, thiophilic, hydrogen bond donating, hydrogen bond accepting, pi-pi bond donating, pi-pi bond accepting, or metal chelating ability of the cross-linked gel is determined under conditions suitable for binding (room temperature, first fluid, see below).

In certain embodiments, the invention relates to any one of the aforementioned composite materials, wherein the cross-linked gel comprises a polymer derived from 2-(diethylamino)ethyl methacrylate, 2-aminoethyl methacrylate, 2-carboxyethyl acrylate, 2-(methylthio)ethyl methacrylate, acrylamide, N-acryloxysuccinimide, butyl acrylate or methacrylate, N,N-diethylacrylamide, N,N-dimethylacrylamide, 2-(N,N-dimethylamino)ethyl acrylate or methacrylate, N-[3-(N,N-dimethylamino)propyl]methacrylamide, N,N-dimethylacrylamide, ethyl acrylate or methacrylate, 2-ethylhexyl methacrylate, hydroxypropyl methacrylate, glycidyl acrylate or methacrylate, ethylene glycol phenyl ether methacrylate, methacrylamide, methacrylic anhydride, propyl acrylate or methacrylate, N-isopropylacrylamide, styrene, 4-vinylpyridine, vinylsulfonic acid, N-vinyl-2-pyrrolidinone (VP), acrylamido-2-methyl-1-propanesulfonic acid, styrenesulfonic acid, alginic acid, (3-acrylamidopropyl)trimethylammonium halide, diallyldimethylammonium halide, 4-vinyl-N-methylpyridinium halide, vinylbenzyl-N-trimethylammonium halide, methacryloxyethyltrimethylammonium halide, 3-sulfopropyl methacrylate, 2-(2-methoxy)ethyl acrylate or methacrylate, hydroxyethyl acrylamide, N-(3-methoxypropyl) acrylamide), N-[tris(hydroxymethyl)methyl]acrylamide, N-phenyl acrylamide, N-tert-butyl acrylamide, or diacetone acrylamide.

In certain embodiments, the invention relates to any one of the aforementioned composite materials, wherein the cross-linked gel comprises a polymer derived from more than one monomer.

In certain embodiments, the invention relates to any one of the aforementioned composite materials, wherein the cross-linked gel comprises a polymer derived from 2-carboxyethyl acrylate, acrylamido-2-methyl-1-propanesulfonic acid, ethylene glycol phenyl ether methacrylate, and 2-(methylthio)ethyl methacrylate. In certain embodiments, the invention relates to any one of the aforementioned methods, wherein the cross-linked gel comprises a polymer derived from 2-carboxyethyl acrylate, acrylamido-2-methyl-1-propanesulfonic acid, ethylene glycol phenyl ether methacrylate, and 2-(methylthio)ethyl methacrylate in a molar ratio of about 1:about 0.2:about 0.1:about 0.06. In certain embodiments, the invention relates to any one of the aforementioned methods, wherein the cross-linked gel comprises a polymer derived from 2-carboxyethyl acrylate, acrylamido-2-methyl-1-propanesulfonic acid, ethylene glycol phenyl ether methacrylate, and 2-(methylthio)ethyl methacrylate in a molar ratio of about 1:about 0.22:about 0.14:about 0.06.

In certain embodiments, the invention relates to any one of the aforementioned composite materials, wherein the cross-linked gel comprises a polymer derived from 2-carboxyethyl acrylate, acrylamido-2-methyl-1-propanesulfonic acid, ethylene glycol phenyl ether methacrylate, and hydroxypropyl methacrylate. In certain embodiments, the invention relates to any one of the aforementioned composite materials, wherein the cross-linked gel comprises a polymer derived from 2-carboxyethyl acrylate, acrylamido-2-methyl-1-propanesulfonic acid, ethylene glycol phenyl ether methacrylate, and hydroxypropyl methacrylate in a molar ratio of about 1:about 0.2:about 0.2:about 0.1. In certain embodiments, the invention relates to any one of the aforementioned composite materials, wherein the cross-linked gel comprises a polymer derived from 2-carboxyethyl acrylate, acrylamido-2-methyl-1-propanesulfonic acid, ethylene glycol phenyl ether methacrylate, and hydroxypropyl methacrylate in a molar ratio of about 1:about 0.25:about 0.15:about 0.14.

In certain embodiments, the invention relates to any one of the aforementioned composite materials, wherein the cross-linked gel comprises a polymer derived from 2-carboxyethyl acrylate, acrylamido-2-methyl-1-propanesulfonic acid, and ethylene glycol phenyl ether methacrylate. In certain embodiments, the invention relates to any one of the aforementioned composite materials, wherein the cross-linked gel comprises a polymer derived from 2-carboxyethyl acrylate, acrylamido-2-methyl-1-propanesulfonic acid, and ethylene glycol phenyl ether methacrylate in a molar ratio of about 1:about 0.3:about 0.1. In certain embodiments, the invention relates to any one of the aforementioned composite materials, wherein the cross-linked gel comprises a polymer derived from 2-carboxyethyl acrylate, acrylamido-2-methyl-1-propanesulfonic acid, and ethylene glycol phenyl ether methacrylate in a molar ratio of about 1:about 0.26:about 0.15.

In certain embodiments, the invention relates to any one of the aforementioned composite materials, wherein the cross-linked gel comprises a polymer derived from vinylbenzyl-N-trimethylammonium halide. In certain embodiments, the invention relates to any one of the aforementioned composite materials, wherein the cross-linked gel comprises a polymer derived from vinylbenzyl-N-trimethylammonium chloride.

In certain embodiments, the invention relates to any one of the aforementioned composite materials, wherein the cross-linked gel comprises a polymer derived from 2-(diethylamino)ethyl methacrylate, (ar-vinylbenzyl)trimethylammonium chloride, ethylene glycol phenyl ether methacrylate, and 2-aminoethyl methacrylate. In certain embodiments, the invention relates to any one of the aforementioned composite materials, wherein the cross-linked gel comprises a polymer derived from 2-(diethylamino)ethyl methacrylate, (ar-vinylbenzyl)trimethylammonium chloride, ethylene glycol phenyl ether methacrylate, and 2-aminoethyl methacrylate in a molar ratio of about 1:about 0.4:about 0.5:about 0.1. In certain embodiments, the invention relates to any one of the aforementioned composite materials, wherein the cross-linked gel comprises a polymer derived from 2-(diethylamino)ethyl methacrylate, (ar-vinylbenzyl)trimethylammonium chloride, ethylene glycol phenyl ether methacrylate, and 2-aminoethyl methacrylate in a molar ratio of about 1:about 0.36:about 0.52:about 0.1.

In certain embodiments, the invention relates to any one of the aforementioned composite materials, wherein the cross-linked gel comprises a polymer derived from 2-acrylamido-2-methyl-1-propanesulfonic acid sodium salt, N-isopropyl acrylamide, and N-phenylacrylamide. In certain embodiments, the invention relates to any one of the aforementioned composite materials, wherein the cross-linked gel comprises a polymer derived from 2-acrylamido-2-methyl-1-propanesulfonic acid sodium salt, N-isopropyl acrylamide, and N-phenylacrylamide in a molar ratio of about 1:about 0.2:about 0.1. In certain embodiments, the invention relates to any one of the aforementioned composite materials, wherein the cross-linked gel comprises a polymer derived from 2-carboxyethyl acrylate, acrylamido-2-methyl-1-propanesulfonic acid, and ethylene glycol phenyl ether methacrylate in a molar ratio of about 1:about 0.18:about 0.1.

In certain embodiments, the invention relates to any one of the aforementioned composite materials, wherein the cross-linked gel comprises a polymer derived from 2-acrylamido-2-methyl-1-propanesulfonic acid sodium salt, N-isopropyl acrylamide (NIPAM) (or N-[tris(hydroxymethyl)methyl]acrylamide (THMAAm) or N-(3-methoxypropyl) acrylamide (MPAAm) or N,N'-dimethylacrylamide (DMAAm)) and N-phenylacrylamide. In certain embodiments, the invention relates to any one of the aforementioned composite materials, wherein the cross-linked gel comprises a polymer derived from 2-acrylamido-2-methyl-1-propanesulfonic acid sodium salt, N-isopropyl acrylamide (NIPAM) (or N-[tris(hydroxymethyl)methyl]acrylamide (THMAAm) or N-(3-methoxypropyl) acrylamide (MPAAm) or N,N'-dimethylacrylamide (DMAAm)) and N-phenylacrylamide in a molar ratio of about 1:about 0.2:about 0.1. In certain embodiments, the invention relates to any one of the aforementioned composite materials, wherein the cross-linked gel comprises a polymer derived from 2-acrylamido-2-methyl-1-propanesulfonic acid sodium salt, N-isopropyl acrylamide (NIPAM) (or N-[tris(hydroxymethyl)methyl]acrylamide (THMAAm) or N-(3-methoxypropyl) acrylamide (MPAAm) or N,N'-dimethylacrylamide (DMAAm)) and N-phenylacrylamide in a molar ratio of about 1:about 0.18:about 0.1

In certain embodiments, the invention relates to any one of the aforementioned composite materials, wherein the cross-linked gel comprises a polymer derived from 2-acrylamido-2-methyl-1-propanesulfonic acid sodium salt, N-isopropyl acrylamide, and ethylene glycol phenyl ether methacrylate. In certain embodiments, the invention relates to any one of the aforementioned composite materials, wherein the cross-linked gel comprises a polymer derived from 2-acrylamido-2-methyl-1-propanesulfonic acid sodium salt, N-isopropyl acrylamide, and ethylene glycol phenyl ether methacrylate in a molar ratio of about 1:about 0.1:about 0.2. In certain embodiments, the invention relates to any one of the aforementioned composite materials, wherein the cross-linked gel comprises a polymer derived from 2-acrylamido-2-methyl-1-propanesulfonic acid sodium salt, N-isopropyl acrylamide, and ethylene glycol phenyl ether methacrylate in a molar ratio of about 1:about 0.1:about 0.15.

In certain embodiments, the invention relates to any one of the aforementioned composite materials, wherein the cross-linking agent is selected from the group consisting of glycerol 1,3-diglycerolate diacrylate, glycerol dimethacrylate, 3-(acryloyloxy)-2-hydroxypropyl methacrylate, glycerol propoxylate triacrylate, bisacrylamidoacetic acid, 2,2-bis[4-(2-acryloxyethoxy)phenyl]propane, 2,2-bis(4-methacryloxyphenyl)propane, butanediol diacrylate and dimethacrylate, 1,4-butanediol divinyl ether, 1,4-cyclohexanediol diacrylate and dimethacrylate, 1,10-dodecanediol diacrylate and dimethacrylate, 1,4-diacryloylpiperazine, diallylphthalate, 2,2-dimethylpropanediol diacrylate and dimethacrylate, dipentaerythritol pentaacrylate, dipropylene glycol diacrylate and dimethacrylate, N,N-dodecamethylenebisacrylamide, divinylbenzene, glycerol trimethacrylate, glycerol tris(acryloxypropyl) ether, N,N'-hexamethylenebisacrylamide, N,N'-octamethylenebisacrylamide, 1,5-pentanediol diacrylate and dimethacrylate, 1,3-phenylenediacrylate, poly(ethylene glycol) diacrylate and dimethacrylate, poly(propylene) diacrylate and dimethacrylate, triethylene glycol diacrylate and dimethacrylate, triethylene glycol divinyl ether, tripropylene glycol diacrylate or dimethacrylate, diallyl diglycol carbonate, poly(ethylene glycol) divinyl ether, N,N'-dimethacryloylpiperazine, divinyl glycol, ethylene glycol diacrylate, ethylene glycol dimethacrylate, N,N'-methylenebisacrylamide, 1,1,1-trimethylolethane trimethacrylate, 1,1,1-trimethylolpropane triacrylate, 1,1,1-trimethylolpropane trimethacrylate (TRIM-M), vinyl acrylate, 1,6-hexanediol diacrylate and dimethacrylate, 1,3-butylene glycol diacrylate and dimethacrylate, alkoxylated cyclohexane dimethanol diacrylate, alkoxylated hexanediol diacrylate, alkoxylated neopentyl glycol diacrylate, aromatic dimethacrylate, caprolactone modified neopentylglycol hydroxypivalate diacrylate, cyclohexane dimethanol diacrylate and dimethacrylate, ethoxylated bisphenol diacrylate and dimethacrylate, neopentyl glycol diacrylate and dimethacrylate, ethoxylated trimethylolpropane triacrylate, propoxylated trimethylolpropane triacrylate, propoxylated glyceryl triacrylate, pentaerythritol triacrylate, tris (2-hydroxy ethyl)isocyanurate triacrylate, di-trimethylolpropane tetraacrylate, dipentaerythritol pentaacrylate, ethoxylated pentaerythritol tetraacrylate, pentaacrylate ester, pentaerythritol tetraacrylate, caprolactone modified dipentaerythritol hexaacrylate, N,N'-methylenebisacrylamide, diethylene glycol diacrylate and dimethacrylate, trimethylolpropane triacrylate, ethylene glycol diacrylate and dimethacrylate, tetra (ethylene glycol) diacrylate, 1,6-hexanediol diacrylate, divinylbenzene, 1,3-butanediol dimethacrylate, poly(ethylene glycol) diacrylate, 1,3,5-triacryloylhexahydro-1,3,5-triazine, trimethylolpropane diallyl ether, 2,4,6-triallyloxy-1, 3,5-triazine, 1,3,5-triallyl-1,3,5-triazine-2,4,6-(1H,3H,5H)-trione, N,N'-hexamethylenebis(methacrylamide), and glyoxal bis(diallylacetal).

In certain embodiments, the invention relates to any one of the aforementioned composite materials, wherein the cross-linking agent is glycerol 1,3-diglycerolate diacrylate.

In certain embodiments, the invention relates to any one of the aforementioned composite materials, wherein the cross-linking agent comprises glycerol dimethacrylate or 3-(acryloyloxy)-2-hydroxypropyl methacrylate. In certain embodiments, the invention relates to any one of the aforementioned composite materials, wherein the cross-linking agent comprises glycerol dimethacrylate and 3-(acryloyloxy)-2-hydroxypropyl methacrylate. In certain embodiments, the invention relates to any one of the aforementioned composite materials, wherein the cross-linking agent comprises glycerol dimethacrylate and 3-(acryloyloxy)-2-hydroxypropyl methacrylate in a molar ratio of about 1:about 0.9.

In certain embodiments, the invention relates to any one of the aforementioned composite materials, wherein the cross-linking agent is glycerol propoxylate triacrylate.

In certain embodiments, the invention relates to any one of the aforementioned composite materials, wherein the cross-linking agent is 1,1,1-trimethylolpropane triacrylate or 1,1,1-trimethylolpropane trimethacrylate.

In certain embodiments, the invention relates to any one of the aforementioned composite materials, wherein the cross-linking agent is N,N-methylenebisacrylamide.

In certain embodiments, the invention relates to any one of the aforementioned composite materials, wherein the cross-linking agent is ethylene glycol dimethacrylate.

In certain embodiments, the invention relates to any one of the aforementioned composite materials, wherein the cross-linking agent is N,N'-hexamethylenebis(methacrylamide).

In certain embodiments, the invention relates to any one of the aforementioned composite materials, wherein the cross-linking agent is 1,3,5-triacryloylhexahydro-1,3,5-triazine.

In certain embodiments, the invention relates to any one of the aforementioned composite materials, wherein the cross-linking agent is 2,4,6-triallyloxy-1,3,5-triazine.

In certain embodiments, the invention relates to any one of the aforementioned composite materials, wherein the cross-linking agent is 1,3,5-triallyl-1,3,5-triazine-2,4,6-(1H,3H,5H)-trione.

In certain embodiments, the invention relates to any one of the aforementioned composite materials, wherein the cross-linking agent is N,N'-hexamethylenebis(methacrylamide).

In certain embodiments, the invention relates to any one of the aforementioned composite materials, wherein the cross-linking agent is glyoxal bis(diallylacetal).

In certain embodiments, the invention relates to any one of the aforementioned composite materials wherein the cross-linked gel comprises macropores; the macroporous cross-linked gel has a volume porosity of about 30% to about 80%; and the macropores have an average pore diameter of about 10 nm to about 3000 nm.

In certain embodiments, the invention relates to any one of the aforementioned composite materials wherein the cross-linked gel comprises macropores; the macroporous cross-linked gel has a volume porosity of about 40% to about 70%. In certain embodiments, the invention relates to any one of the aforementioned composite materials wherein the cross-linked gel comprises macropores; the macroporous cross-linked gel has a volume porosity of about 40%, about 45%, about 50%, about 55%, about 60%, about 65%, or about 70%.

In certain embodiments, the invention relates to any one of the aforementioned composite materials, wherein the average pore diameter of the macropores is about 25 nm to about 1500 nm.

In certain embodiments, the invention relates to any one of the aforementioned composite materials, wherein the average pore diameter of the macropores is about 50 nm to about 1000 nm. In certain embodiments, the invention relates to any one of the aforementioned composite materials, wherein the average pore diameter of the macropores is about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, or about 700 nm.

In certain embodiments, the invention relates to any one of the aforementioned composite materials, wherein the average pore diameter of the macropores is from about 300 nm to about 400 nm.

In certain embodiments, the invention relates to any one of the aforementioned composite materials, wherein the composite material is a membrane.

In certain embodiments, the invention relates to any one of the aforementioned composite materials, wherein the support member has a void volume; and the void volume of the support member is substantially filled with the macroporous cross-linked gel.

In certain embodiments, the invention relates to any one of the aforementioned composite materials, wherein the support member comprises a polymer; the support member is about 10 μm to about 500 μm thick; the pores of the support member have an average pore diameter of about 0.1 μm to about 25 μm; and the support member has a volume porosity of about 40% to about 90%.

In certain embodiments, the invention relates to any one of the aforementioned composite materials, wherein the thickness of the support member is about 10 μm to about 1000 μm. In certain embodiments, the invention relates to any one of the aforementioned composite materials, wherein the thickness of the support member is about 10 μm to about 500 μm. In certain embodiments, the invention relates to any one of the aforementioned composite materials, wherein the thickness of the support member is about 30 μm to about 300 μm. In certain embodiments, the invention relates to any one of the aforementioned composite materials, wherein the thickness of the support member is about 30 μm, about 50 μm, about 100 μm, about 150 μm, about 200 μm, about 250 μm, or about 300 μm.

In certain embodiments, the invention relates to any one of the aforementioned composite materials, wherein the pores of the support member have an average pore diameter of about 0.1 μm to about 25 μm. In certain embodiments, the invention relates to any one of the aforementioned composite materials, wherein the pores of the support member have an average pore diameter of about 0.5 μm to about 15 μm. In certain embodiments, the invention relates to any one of the aforementioned composite materials, wherein the pores of the support member have an average pore diameter of about 0.5 μm, about 1 μm, about 2 μm, about 3 μm, about 4 μm, about 5 μm, about 6 μm, about 7 μm, about 8 μm, about 9 μm, about 10 μm, about 11 μm, about 12 μm, about 13 μm, about 14 μm, or about 15 μm.

In certain embodiments, the invention relates to any one of the aforementioned composite materials, wherein the support member has a volume porosity of about 40% to about 90%. In certain embodiments, the invention relates to any one of the aforementioned composite materials, wherein the support member has a volume porosity of about 50% to about 80%. In certain embodiments, the invention relates to any one of the aforementioned composite materials, wherein the support member has a volume porosity of about 50%, about 60%, about 70%, or about 80%.

In certain embodiments, the invention relates to any one of the aforementioned composite materials, wherein the support member comprises a polyolefin.

In certain embodiments, the invention relates to any one of the aforementioned composite materials, wherein the support member comprises a polymeric material selected from the group consisting of polysulfones, polyethersulfones, polyphenyleneoxides, polycarbonates, polyesters, cellulose and cellulose derivatives.

In certain embodiments, the invention relates to any one of the aforementioned composite materials, wherein the support member comprises a fibrous woven or non-woven fabric comprising a polymer; the support member is from about 10 µm to about 2000 µm thick; the pores of the support member have an average pore diameter of from about 0.1 µm to about 25 µm; and the support member has a volume porosity of about 40% to about 90%.

Exemplary Methods

In certain embodiments, the invention relates to a method, comprising the step of:
  contacting at a first flow rate a first fluid comprising a substance with any one of the aforementioned composite materials, thereby adsorbing or absorbing a portion of the substance onto the composite material.

In certain embodiments, the first fluid further comprises a fragmented antibody, aggregated antibodies, a host cell protein, a polynucleotide, an endotoxin, or a virus.

In certain embodiments, the invention relates to any one of the aforementioned methods, wherein the fluid flow path of the first fluid is substantially through the macropores of the composite material.

In certain embodiments, the invention relates to any one of the aforementioned methods, further comprising the step of:
  contacting at a second flow rate a second fluid with the substance adsorbed or absorbed onto the composite material, thereby releasing a first portion of the substance from the composite material.

In certain embodiments, the invention relates to any one of the aforementioned methods, wherein the fluid flow path of the second fluid is substantially through the macropores of the composite material.

In certain embodiments, the invention relates to any one of the aforementioned methods, further comprising the step of:
  contacting at a third flow rate a third fluid with the substance adsorbed or absorbed onto the composite material, thereby releasing a second portion of the substance from the composite material.

In certain embodiments, the invention relates to any one of the aforementioned methods, wherein the substance is a biological molecule or biological ion.

In certain embodiments, the invention relates to any one of the aforementioned methods, wherein the biological molecule or biological ion is selected from the group consisting of albumins, lysozyme, viruses, cells, γ-globulins of human and animal origins, immunoglobulins of human and animal origins, proteins of recombinant and natural origins, polypeptides of synthetic and natural origins, interleukin-2 and its receptor, enzymes, monoclonal antibodies, trypsin and its inhibitor, cytochrome C, myoglobin, myoglobulin, α-chymotrypsinogen, recombinant human interleukin, recombinant fusion protein, nucleic acid derived products, DNA of synthetic and natural origins, and RNA of synthetic and natural origins.

In certain embodiments, the invention relates to any one of the aforementioned methods, wherein the biological molecule or biological ion is lysozyme, hIgG, myoglobin, human serum albumin, soy trypsin inhibitor, transferring, enolase, ovalbumin, ribonuclease, egg trypsin inhibitor, cytochrome c, Annexin V, or α-chymotrypsinogen.

In certain embodiments, the invention relates to any one of the aforementioned methods, wherein the first fluid is a buffer. In certain embodiments, the invention relates to any one of the aforementioned methods, wherein the concentration of the buffer in the first fluid is about 20 mM, about 30 mM, about 40 mM, about 50 mM, about 60 mM, about 70 mM, about 75 mM, about 80 mM, about 85 mM, about 90 mM, about 95 mM, about 0.1 M, about 0.11 M, about 0.12 M, about 0.13 M, about 0.14 M, about 0.15 M, about 0.16 M, about 0.17 M, about 0.18 M, about 0.19 M or about 0.2 M. In certain embodiments, the invention relates to any one of the aforementioned methods, wherein the pH of the first fluid is about 2, about 2.5, about 3, about 3.5, about 4, about 4.5, about 5, about 5.5, about 6, about 7, about 8, or about 9.

In certain embodiments, the invention relates to any one of the aforementioned methods, wherein the first fluid comprises sodium acetate. In certain embodiments, the invention relates to any one of the aforementioned methods, wherein the first fluid comprises sodium citrate. In certain embodiments, the invention relates to any one of the aforementioned methods, wherein the first fluid comprises sodium phosphate.

In certain embodiments, the invention relates to any one of the aforementioned methods, wherein the first fluid comprises a salt. In certain embodiments, the invention relates to any one of the aforementioned methods, wherein the salt is selected from the group consisting of glycine-HCl, NaCl, and $NH_4Cl$. In certain embodiments, the invention relates to any one of the aforementioned methods, wherein the first fluid comprises sodium chloride. In certain embodiments, the invention relates to any one of the aforementioned methods, wherein the first fluid comprises sodium chloride in a concentration of about 10 mM to about 600 mM. In certain embodiments, the invention relates to any one of the aforementioned methods, wherein the first fluid comprises sodium chloride in a concentration of about 50 mM, about 75 mM, about 100 mM, about 125 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, about 500 mM, or about 525 mM.

In certain embodiments, the invention relates to any one of the aforementioned methods, wherein the first fluid is a clarified cell culture supernatant.

In certain embodiments, the invention relates to any one of the aforementioned methods, wherein the concentration of the substance in the first fluid is about 0.2 mg/mL to about 10 mg/mL. In certain embodiments, the invention relates to any one of the aforementioned methods, wherein the concentration of the substance in the first fluid is about 0.2 mg/mL, about 0.4 mg/mL, about 0.6 mg/mL, about 0.8 mg/mL, about 1 mg/mL, about 2 mg/mL, about 3 mg/mL, about 4 mg/mL, about 5 mg/mL, about 6 mg/mL, about 7 mg/mL, about 8 mg/mL, about mg/mL, or about 10 mg/mL.

In certain embodiments, the invention relates to any one of the aforementioned methods, wherein the first flow rate is up to about 50 bed volumes/min. In certain embodiments, the invention relates to any one of the aforementioned methods, wherein the first flow rate is about 5 bed volumes/min, about 10 bed volumes/min, about 20 bed volumes/min, about 30 bed volumes/min, about 40 bed volumes/min, or about 50 bed volumes/min.

In certain embodiments, the invention relates to any one of the aforementioned methods, wherein the first flow rate is about 0.5 mL/min to about 2 mL/min. In certain embodiments, the invention relates to any one of the aforementioned methods, wherein the first flow rate is about 0.5 mL/min, about 0.6 mL/min, about 0.7 mL/min, about 0.8 mL/min, about 0.9 mL/min, about 1 mL/min, about 1.1 mL/min, about 1.2 mL/min, about 1.3 mL/min, about 1.4 mL/min, about 1.5 mL/min, about 1.6 mL/min, about 1.7 mL/min, or about 1.8 mL/min.

In certain embodiments, the invention relates to any one of the aforementioned methods, wherein the second fluid is a buffer. In certain embodiments, the invention relates to any one of the aforementioned methods, wherein the second fluid comprises 2-(N-morpholino)ethanesulfonic acid. In certain embodiments, the invention relates to any one of the aforementioned methods, wherein the second fluid comprises 2-(N-morpholino)ethanesulfonic acid in a concentration of about 50 mM to about 150 mM. In certain embodiments, the invention relates to any one of the aforementioned methods, wherein the second fluid comprises 2-(N-morpholino)ethanesulfonic acid in about 50 mM, about 60 mM, about 70 mM, about 80 mM, about 90 mM, about 100 mM, about 110 mM, about 120 mM, about 130 mM, about 140 mM, or about 150 mM.

In certain embodiments, the invention relates to any one of the aforementioned methods, wherein the pH of the second fluid is about 4 to about 8. In certain embodiments, the invention relates to any one of the aforementioned methods, wherein the pH of the second fluid is about 5, about 5.2, about 5.4, about 5.5, about 5.6, about 5.7, about 5.8, about 5.9, about 6, about 6.2, or about 6.4.

In certain embodiments, the invention relates to any one of the aforementioned methods, wherein the second fluid comprises a salt. In certain embodiments, the invention relates to any one of the aforementioned methods, wherein the salt is selected from the group consisting of glycine-HCl, NaCl, and $NH_4Cl$. In certain embodiments, the invention relates to any one of the aforementioned methods, wherein the salt concentration in the second fluid is about 70 mM to about 200 mM. In certain embodiments, the invention relates to any one of the aforementioned methods, wherein the salt concentration is about 70 mM, about 80 mM, about 90 mM, about 100 mM, about 110 mM, about 115 mM, about 120 mM, about 125 mM, about 130 mM, about 135 mM, about 140 mM, about 145 mM, about 150 mM, about 160 mM, about 170 mM, about 180 mM, about 190 mM, or about 200 mM.

In certain embodiments, the invention relates to any one of the aforementioned methods, wherein the third fluid is a buffer. In certain embodiments, the invention relates to any one of the aforementioned methods, wherein the third fluid comprises 2-amino-2-hydroxymethyl-propane-1,3-diol/HCl (TRIS/HCl). In certain embodiments, the invention relates to any one of the aforementioned methods, wherein the third fluid comprises 2-amino-2-hydroxymethyl-propane-1,3-diol/HCl (TRIS/HCl) in a concentration of about 15 mM to about 40 mM. In certain embodiments, the invention relates to any one of the aforementioned methods, wherein the third fluid comprises 2-amino-2-hydroxymethyl-propane-1,3-diol/HCl (TRIS/HCl) in about 15 mM, about 20 mM, about 25 mM, about 30 mM, about 35 mM, or about 40 mM.

In certain embodiments, the invention relates to any one of the aforementioned methods, wherein the pH of the third fluid is about 7 to about 9. In certain embodiments, the invention relates to any one of the aforementioned methods, wherein the pH of the third fluid is about 7, about 7.2, about 7.4, about 7.6, about 7.8, about 8, about 8.1, about 8.2, about 8.3, about 8.4, about 8.6, about 8.8, or about 9.

In certain embodiments, the invention relates to any one of the aforementioned methods, wherein the third fluid comprises a salt. In certain embodiments, the invention relates to any one of the aforementioned methods, wherein the salt is selected from the group consisting of glycine-HCl, NaCl, and $NH_4Cl$. In certain embodiments, the invention relates to any one of the aforementioned methods, wherein the salt concentration in the second fluid is about 125 mM to about 400 mM. In certain embodiments, the invention relates to any one of the aforementioned methods, wherein the salt concentration is about 125 mM, about 150 mM, about 175 mM, about 200 mM, about 225 mM, about 250 mM, about 275 mM, about 300 mM, about 325 mM, about 350 mM, about 375 mM, or about 400 mM.

In certain embodiments, the invention relates to any one of the aforementioned methods, further comprising the steps of:
cleaning the composite material; and
repeating the above-mentioned steps.

In certain embodiments, the invention relates to any one of the aforementioned methods, wherein substantially all of the substance is adsorbed or absorbed onto the composite material.

In certain embodiments, the invention relates to a method, comprising the step of:
contacting at a first flow rate a first fluid comprising a substance and an unwanted material with any one of the aforementioned composite materials, thereby adsorbing or absorbing a portion of the unwanted material onto the composite material.

In certain embodiments, the invention relates to any one of the aforementioned methods, wherein the unwanted material comprises a fragmented antibody, aggregated antibodies, a host cell protein, a polynucleotide, an endotoxin, or a virus.

In certain embodiments, the invention relates to any one of the aforementioned methods, wherein substantially all of the unwanted material is adsorbed or absorbed onto the composite material.

In certain embodiments, the invention relates to any one of the aforementioned methods, wherein the fluid flow path of the first fluid is substantially through the macropores of the composite material.

In certain embodiments, the invention relates to any one of the aforementioned methods, wherein the substance is a biological molecule or biological ion.

In certain embodiments, the invention relates to any one of the aforementioned methods, wherein the biological molecule or biological ion is selected from the group consisting of albumins, lysozyme, viruses, cells, γ-globulins of human and animal origins, immunoglobulins of human and animal origins, proteins of recombinant and natural origins, polypeptides of synthetic and natural origins, interleukin-2 and its receptor, enzymes, monoclonal antibodies, trypsin and its inhibitor, cytochrome C, myoglobin, myoglobulin, α-chymotrypsinogen, recombinant human interleukin, recombinant fusion protein, nucleic acid derived products, DNA of synthetic and natural origins, and RNA of synthetic and natural origins.

In certain embodiments, the invention relates to any one of the aforementioned methods, wherein the biological molecule or biological ion is lysozyme, hIgG, myoglobin, human serum albumin, soy trypsin inhibitor, transferring, enolase, ovalbumin, ribonuclease, egg trypsin inhibitor, cytochrome c, Annexin V, or α-chymotrypsinogen.

In certain embodiments, the invention relates to any one of the aforementioned methods, wherein the first fluid is a buffer. In certain embodiments, the invention relates to any one of the aforementioned methods, wherein the concentration of the buffer in the first fluid is about 20 mM, about 30 mM, about 40 mM, about 50 mM, about 60 mM, about 70 mM, about 75 mM, about 80 mM, about 85 mM, about 90 mM, about 95 mM, about 0.1 M, about 0.11 M, about 0.12 M, about 0.13 M, about 0.14 M, about 0.15 M, about 0.16 M, about 0.17 M, about 0.18 M, about 0.19 M or about 0.2 M.

In certain embodiments, the invention relates to any one of the aforementioned methods, wherein the first fluid comprises sodium acetate. In certain embodiments, the invention relates to any one of the aforementioned methods, wherein the first fluid comprises sodium citrate. In certain embodiments, the invention relates to any one of the aforementioned methods, wherein the first fluid comprises sodium phosphate.

In certain embodiments, the invention relates to any one of the aforementioned methods, wherein the first fluid comprises a salt. In certain embodiments, the invention relates to any one of the aforementioned methods, wherein the salt is selected from the group consisting of glycine-HCl, NaCl, and NH$_4$Cl. In certain embodiments, the invention relates to any one of the aforementioned methods, wherein the first fluid comprises sodium chloride. In certain embodiments, the invention relates to any one of the aforementioned methods, wherein the first fluid comprises sodium chloride in a concentration of about 10 mM to about 600 mM. In certain embodiments, the invention relates to any one of the aforementioned methods, wherein the first fluid comprises sodium chloride in a concentration of about 50 mM, about 75 mM, about 100 mM, about 125 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, about 500 mM, or about 525 mM.

In certain embodiments, the invention relates to any one of the aforementioned methods, wherein the first flow rate is about 0.5 mL/min to about 2 mL/min. In certain embodiments, the invention relates to any one of the aforementioned methods, wherein the first flow rate is about 0.5 mL/min, about 0.6 mL/min, about 0.7 mL/min, about 0.8 mL/min, about 0.9 mL/min, about 1 mL/min, about 1.1 mL/min, about 1.2 mL/min, about 1.3 mL/min, about 1.4 mL/min, about 1.5 mL/min, about 1.6 mL/min, about 1.7 mL/min, or about 1.8 mL/min.

In certain embodiments, the invention relates to any one of the aforementioned methods, wherein the first fluid is a clarified cell culture supernatant.

In certain embodiments, the invention relates to a method of making a composite material, comprising the steps of:

combining a first monomer, a photoinitiator, a cross-linking agent, and a solvent, thereby forming a monomeric mixture;

contacting a support member with the monomeric mixture, thereby forming a modified support member; wherein the support member comprises a plurality of pores extending through the support member, and the average pore diameter of the pores is about 0.1 to about 25 μm;

covering the modified support member with a polymeric sheet, thereby forming a covered support member; and irradiating the covered support member for a period of time, thereby forming a composite material.

In certain embodiments, the invention relates to any one of the aforementioned methods, wherein the monomeric mixture comprises a plurality of different monomers. In certain embodiments, the invention relates to any one of the aforementioned methods, wherein the monomeric mixture comprises a first monomer and a second monomer. In certain embodiments, the invention relates to any one of the aforementioned methods, wherein the monomeric mixture further comprises a third, fourth, fifth, sixth, seventh, eighth, or ninth monomer.

In certain embodiments, the invention relates to any one of the aforementioned methods, further comprising the step of washing the composite material with a second solvent, thereby forming a washed composite material. In certain embodiments, the second solvent is water.

In certain embodiments, the invention relates to any one of the aforementioned methods, further comprising the step of contacting the composite material or the washed composite material with a salt solution.

In certain embodiments, the salt solution comprises sodium. In certain embodiments, the salt solution comprises sodium hydroxide. In certain embodiments, the salt solution comprises sodium hydroxide in a concentration of about 0.05 N to about 0.15 N. In certain embodiments, the salt solution comprises sodium hydroxide at about 0.06 N, about 0.07 N, about 0.08 N, about 0.09 N, about 0.1 N, about 0.11 N, about 0.12 N, about 0.13 N, or about 0.14 N.

In certain embodiments, the salt solution comprises sodium chloride. In certain embodiments, the salt solution comprises sodium chloride in a concentration of about 0.05 N to about 0.5 N. In certain embodiments, the salt solution comprises sodium chloride in about 0.06 N, about 0.07 N, about 0.08 N, about 0.09 N, about 0.1 N, about 0.11 N, about 0.12 N, about 0.13 N, about 0.14 N, about 0.15 N, about 0.18 N, about 0.2 N, about 0.22 N, about 0.24 N, about 0.26 N, about 0.28 N, about 0.3 N, about 0.32 N, about 0.34 N, about 0.36 N, about 0.38 N, about 0.4 N, about 0.42 N, about 0.44 N, about 0.46 N, about 0.48 N, or about 0.5 N.

In certain embodiments, the salt solution comprises sodium hydroxide and sodium chloride.

In certain embodiments, the invention relates to any one of the aforementioned methods, further comprising the step of removing any excess monomeric mixture from the covered support member.

In certain embodiments, the invention relates to any one of the aforementioned methods, wherein the monomer mixture comprises 2-(diethylamino)ethyl methacrylate, 2-aminoethyl methacrylate, 2-carboxyethyl acrylate, 2-(methylthio)ethyl methacrylate, acrylamide, N-acryloxysuccinimide, butyl acrylate or methacrylate, N,N-diethylacrylamide, N,N-dimethylacrylamide, 2-(N,N-dimethylamino)ethyl acrylate or methacrylate, N-[3-(N,N-dimethylamino)propyl]methacrylamide, N,N-dimethylacrylamide, n-dodecyl acrylate, n-dodecyl methacrylate, ethyl acrylate or methacrylate, 2-ethylhexyl methacrylate, hydroxypropyl methacrylate, glycidyl acrylate or methacrylate, ethylene glycol phenyl ether methacrylate, methacrylamide, methacrylic anhydride, propyl acrylate or methacrylate, N-isopropylacrylamide, styrene, 4-vinylpyridine, vinylsulfonic acid, N-vinyl-2-pyrrolidinone (VP), acrylamido-2-methyl-1-propanesulfonic acid, styrenesulfonic acid, alginic acid, (3-acrylamidopropyl)trimethylammonium halide, diallyldimethylammonium halide, 4-vinyl-N-methylpyridinium halide, vinylbenzyl-N-trimethylammonium halide, methacryloxyethyltrimethylammonium halide, 3-sulfopropyl methacrylate, 2-(2-methoxy)ethyl acrylate or methacrylate, hydroxyethyl acrylamide, N-(3-methoxypropyl acrylamide), N-[tris(hydroxymethyl)methyl]acrylamide, N-phenyl acrylamide, N-tert-butyl acrylamide, or diacetone acrylamide.

In certain embodiments, the invention relates to any one of the aforementioned methods, wherein the monomer mixture comprises more than one monomer. In certain embodiments, the invention relates to any one of the aforementioned methods, wherein the monomer mixture further comprises a second monomer.

In certain embodiments, the invention relates to any one of the aforementioned methods, wherein the monomer mixture comprises 2-carboxyethyl acrylate, acrylamido-2-methyl-1-propanesulfonic acid, ethylene glycol phenyl ether methacrylate, and 2-(methylthio)ethyl methacrylate. In certain embodiments, the invention relates to any one of the aforementioned methods, wherein the monomer mixture comprises 2-carboxyethyl acrylate, acrylamido-2-methyl-1-propanesulfonic acid, ethylene glycol phenyl ether methacrylate, and 2-(methylthio)ethyl methacrylate in a molar ratio of about 1:about 0.2:about 0.1:about 0.06. In certain embodiments, the invention relates to any one of the aforementioned methods, wherein the monomer mixture comprises 2-carboxyethyl acrylate, acrylamido-2-methyl-1-propanesulfonic acid, ethylene glycol phenyl ether methacrylate, and 2-(methylthio)ethyl methacrylate in a molar ratio of about 1:about 0.22:about 0.14:about 0.06.

In certain embodiments, the invention relates to any one of the aforementioned methods, wherein the monomer mixture comprises 2-carboxyethyl acrylate, acrylamido-2-methyl-1-propanesulfonic acid, ethylene glycol phenyl ether methacrylate, and hydroxypropyl methacrylate. In certain embodiments, the invention relates to any one of the aforementioned methods, wherein the monomer mixture comprises 2-carboxyethyl acrylate, acrylamido-2-methyl-1-propanesulfonic acid, ethylene glycol phenyl ether methacrylate, and hydroxypropyl methacrylate in a molar ratio of about 1:about 0.2:about 0.2:about 0.1. In certain embodiments, the invention relates to any one of the aforementioned methods, wherein the monomer mixture comprises 2-carboxyethyl acrylate, acrylamido-2-methyl-1-propanesulfonic acid, ethylene glycol phenyl ether methacrylate, and hydroxypropyl methacrylate in a molar ratio of about 1:about 0.25:about 0.15:about 0.14.

In certain embodiments, the invention relates to any one of the aforementioned methods, wherein the monomer mixture comprises 2-carboxyethyl acrylate, acrylamido-2-methyl-1-propanesulfonic acid, and ethylene glycol phenyl ether methacrylate. In certain embodiments, the invention relates to any one of the aforementioned methods, wherein the monomer mixture comprises 2-carboxyethyl acrylate, acrylamido-2-methyl-1-propanesulfonic acid, and ethylene glycol phenyl ether methacrylate in a molar ratio of about 1:about 0.3:about 0.1. In certain embodiments, the invention relates to any one of the aforementioned methods, wherein the monomer mixture comprises 2-carboxyethyl acrylate, acrylamido-2-methyl-1-propanesulfonic acid, and ethylene glycol phenyl ether methacrylate in a molar ratio of about 1:about 0.26:about 0.15.

In certain embodiments, the invention relates to any one of the aforementioned methods, wherein the monomer mixture comprises vinylbenzyl-N-trimethylammonium halide. In certain embodiments, the invention relates to any one of the aforementioned methods, wherein the monomer mixture comprises vinylbenzyl-N-trimethylammonium chloride.

In certain embodiments, the invention relates to any one of the aforementioned methods, wherein the monomer mixture comprises 2-(diethylamino)ethyl methacrylate, (ar-vinylbenzyl)trimethylammonium chloride, ethylene glycol phenyl ether methacrylate, and 2-aminoethyl methacrylate. In certain embodiments, the invention relates to any one of the aforementioned methods, wherein the monomer mixture comprises 2-(diethylamino)ethyl methacrylate, (ar-vinylbenzyl)trimethylammonium chloride, ethylene glycol phenyl ether methacrylate, and 2-aminoethyl methacrylate in a molar ratio of about 1:about 0.4:about 0.5:about 0.1. In certain embodiments, the invention relates to any one of the aforementioned methods, wherein the monomer mixture comprises 2-(diethylamino)ethyl methacrylate, (ar-vinylbenzyl)trimethylammonium chloride, ethylene glycol phenyl ether methacrylate, and 2-aminoethyl methacrylate in a molar ratio of about 1:about 0.36:about 0.52:about 0.1.

In certain embodiments, the invention relates to any one of the aforementioned methods, wherein the monomers are present in the solvent in about 6% to about 38% (w/w), collectively.

In certain embodiments, the invention relates to any one of the aforementioned methods, wherein the monomers are present in the solvent in an amount of about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, or about 38% (w/w), collectively.

In certain embodiments, the invention relates to any one of the aforementioned methods, wherein the photoinitiator is present in the monomeric mixture in an amount of about 0.4% (w/w) to about 2.5% (w/w) relative to the total weight of monomer.

In certain embodiments, the invention relates to any one of the aforementioned methods, wherein the photoinitiator is present in the monomeric mixture in about 0.6%, about 0.8%, about 1.0%, about 1.2%, or about 1.4% (w/w) relative to the total weight of monomer.

In certain embodiments, the invention relates to any one of the aforementioned methods, wherein the photoinitiator is selected from the group consisting of 1-[4-(2-hydroxyethoxy)-phenyl]-2-hydroxy-2-methyl-1-propane-1-one, 2,2-dimethoxy-2-phenylacetophenone, benzophenone, benzoin and benzoin ethers, dialkoxyacetophenones, hydroxyalkylphenones, and α-hydroxymethyl benzoin sulfonic esters.

In certain embodiments, the invention relates to any one of the aforementioned methods, wherein the solvent comprises 1,3-butanediol, di(propylene glycol) propyl ether, N,N-dimethylacetamide, di(propylene glycol) dimethyl ether, 1,2-propanediol, di(propylene glycol) methyl ether acetate (DPMA), water, dioxane, dimethylsulfoxide (DMSO), dimethylformamide (DMF), acetone, ethanol, N-methylpyrrolidone (NMP), tetrahydrofuran (THF), ethyl acetate, acetonitrile, N-methylacetamide, propanol, tri(propylene glycol) propyl ether, or methanol.

In certain embodiments, the invention relates to any one of the aforementioned methods, wherein the solvent comprises N,N-dimethylacetamide, di(propylene glycol) dimethyl ether, 1,2-propanediol, and water.

In certain embodiments, the invention relates to any one of the aforementioned methods, wherein the solvent comprises N,N-dimethylacetamide. In certain embodiments, the invention relates to any one of the aforementioned methods, wherein the solvent comprises N,N-dimethylacetamide in an amount of about 15% to about 40% by weight. In certain embodiments, the invention relates to any one of the aforementioned methods, wherein the solvent comprises N,N-dimethylacetamide in about 20%, about 21%, about 22%, about 23%, about 24%, about 25%, about 26%, about 27%, about 28%, about 29%, about 30%, about 31%, about 32%, about 33%, about 34%, or about 35% by weight.

In certain embodiments, the invention relates to any one of the aforementioned methods, wherein the solvent comprises di(propylene glycol) dimethyl ether. In certain embodiments, the invention relates to any one of the aforementioned methods, wherein the solvent comprises di(propylene glycol) dimethyl ether in an amount of about 30% to about 90% by weight. In certain embodiments, the invention relates to any one of the aforementioned methods, wherein the solvent comprises di(propylene glycol) dimethyl ether in about 40%, about 42%, about 44%, about 46%, about 48%, about 50%, about 52%, about 54%, about 56%, about 58%, about 60%, about 62%, about 64%, about 66%, about 68%, about 70%, about 72%, about 74%, about 76%, about 78%, or about 80% by weight.

In certain embodiments, the invention relates to any one of the aforementioned methods, wherein the solvent comprises 1,2-propanediol. In certain embodiments, the invention relates to any one of the aforementioned methods, wherein the solvent comprises 1,2-propanediol in an amount of about 3% to about 75% by weight. In certain embodiments, the invention relates to any one of the aforementioned methods, wherein the solvent comprises 1,2-propanediol in about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, or about 75% by weight.

In certain embodiments, the invention relates to any one of the aforementioned methods, wherein the solvent comprises water. In certain embodiments, the invention relates to any one of the aforementioned methods, wherein the solvent comprises water in an amount of about 2% to about 9% by weight. In certain embodiments, the invention relates to any one of the aforementioned methods, wherein the solvent comprises water in about 2%, about 3%, about 4%, about 5%, about 6%, about 7%, about 8%, or about 9% by weight.

In certain embodiments, the invention relates to any one of the aforementioned methods, wherein the solvent comprises di(propylene glycol) methyl ether acetate. In certain embodiments, the invention relates to any one of the aforementioned methods, wherein the solvent comprises di(propylene glycol) methyl ether acetate in an amount of about 24% to about 72% by weight. In certain embodiments, the invention relates to any one of the aforementioned methods, wherein the solvent comprises di(propylene glycol) methyl ether acetate in about 30%, about 32%, about 34%, about 36%, about 38%, about 40%, about 42%, about 44%, about 46%, about 48%, about 50%, about 52%, about 54%, about 56%, about 58%, about 60%, about 62%, about 64%, or about 66% by weight.

In certain embodiments, the invention relates to any one of the aforementioned methods, wherein the solvent comprises 1,3-butanediol. In certain embodiments, the invention relates to any one of the aforementioned methods, wherein the solvent comprises 1,3-butanediol in an amount of about 35% to about 95% by weight. In certain embodiments, the invention relates to any one of the aforementioned methods, wherein the solvent comprises 1,3-butanediol in about 40%, about 45%, about 50%, about 55%, about 60%, about 65%, about 70%, about 75%, about 80%, about 85%, or about 90% by weight.

In certain embodiments, the invention relates to any one of the aforementioned methods, wherein the cross-linking agent is present in the solvent in about 4% to about 25% (w/w).

In certain embodiments, the invention relates to any one of the aforementioned methods, wherein the cross-linking agent is present in the solvent in an amount of about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% (w/w).

In certain embodiments, the invention relates to any one of the aforementioned methods, wherein the cross-linking agent is selected from the group consisting of glycerol 1,3-diglycerolate diacrylate, glycerol dimethacrylate, 3-(acryloyloxy)-2-hydroxypropyl methacrylate, glycerol propoxylate triacrylate, bisacrylamidoacetic acid, 2,2-bis[4-(2-acryloxyethoxy)phenyl]propane, 2,2-bis(4-methacryloxyphenyl)propane, butanediol diacrylate and dimethacrylate, 1,4-butanediol divinyl ether, 1,4-cyclohexanediol diacrylate and dimethacrylate, 1,10-dodecanediol diacrylate and dimethacrylate, 1,4-diacryloylpiperazine, diallylphthalate, 2,2-dimethylpropanediol diacrylate and dimethacrylate, dipentaerythritol pentaacrylate, dipropylene glycol diacrylate and dimethacrylate, N,N-dodecamethylenebisacrylamide, divinylbenzene, glycerol trimethacrylate, glycerol tris(acryloxypropyl) ether, N,N'-hexamethylenebisacrylamide, N,N'-octamethylenebisacrylamide, 1,5-pentanediol diacrylate and dimethacrylate, 1,3-phenylenediacrylate, poly(ethylene glycol) diacrylate and dimethacrylate, poly(propylene) diacrylate and dimethacrylate, triethylene glycol diacrylate and dimethacrylate, triethylene glycol divinyl ether, tripropylene glycol diacrylate or dimethacrylate, diallyl diglycol carbonate, poly(ethylene glycol) divinyl ether, N,N'-dimethacryloylpiperazine, divinyl glycol, ethylene glycol diacrylate, ethylene glycol dimethacrylate, N,N'-methylenebisacrylamide, 1,1,1-trimethylolethane trimethacrylate, 1,1,1-trimethylolpropane triacrylate, 1,1,1-trimethylolpropane trimethacrylate (TRIM-M), vinyl acrylate, 1,6-hexanediol diacrylate and dimethacrylate, 1,3-butylene glycol diacrylate and dimethacrylate, alkoxylated cyclohexane dimethanol diacrylate, alkoxylated hexanediol diacrylate, alkoxylated neopentyl glycol diacrylate, aromatic dimethacrylate, caprolactone modified neopentylglycol hydroxypivalate diacrylate, cyclohexane dimethanol diacrylate and dimethacrylate, ethoxylated bisphenol diacrylate and dimethacrylate, neopentyl glycol diacrylate and dimethacrylate, ethoxylated trimethylolpropane triacrylate, propoxylated trimethylolpropane triacrylate, propoxylated glyceryl triacrylate, pentaerythritol triacrylate, tris (2-hydroxy ethyl)isocyanurate triacrylate, di-trimethylolpropane tetraacrylate, dipentaerythritol pentaacrylate, ethoxylated pentaerythritol tetraacrylate, pentaacrylate ester, pentaerythritol tetraacrylate, caprolactone modified dipentaerythritol hexaacrylate, N,N'-methylenebisacrylamide, diethylene glycol diacrylate and dimethacrylate, trimethylolpropane triacrylate, ethylene glycol diacrylate and dimethacrylate, tetra(ethylene glycol) diacrylate, 1,6-hexanediol diacrylate, divinylbenzene, poly(ethylene glycol) diacrylate, 1,3,5-triacryloylhexahydro-1,3,5-triazine, trimethylolpropane diallyl ether, 2,4,6-triallyloxy-1,3,5-triazine, 1,3,5-triallyl-1,3,5-triazine-2,4,6-(1H,3H,5H)-trione, N,N'-hexamethylenebis(methacrylamide), and glyoxal bis(diallylacetal).

In certain embodiments, the invention relates to any one of the aforementioned methods, wherein the cross-linking agent is glycerol 1,3-diglycerolate diacrylate.

In certain embodiments, the invention relates to any one of the aforementioned methods, wherein the cross-linking agent comprises glycerol dimethacrylate or 3-(acryloyloxy)-2-hydroxypropyl methacrylate. In certain embodiments, the invention relates to any one of the aforementioned methods, wherein the cross-linking agent comprises glycerol dimethacrylate and 3-(acryloyloxy)-2-hydroxypropyl methacrylate. In certain embodiments, the invention relates to any one of the aforementioned methods, wherein the cross-linking agent comprises glycerol dimethacrylate and 3-(acryloyloxy)-2-hydroxypropyl methacrylate in a molar ratio of about 1:about 0.9.

In certain embodiments, the invention relates to any one of the aforementioned methods, wherein the cross-linking agent is glycerol propoxylate triacrylate.

In certain embodiments, the invention relates to any one of the aforementioned methods, wherein the cross-linking agent is 1,1,1-trimethylolpropane triacrylate or 1,1,1-trimethylolpropane trimethacrylate.

In certain embodiments, the invention relates to any one of the aforementioned methods, wherein the cross-linking agent is ethylene glycol dimethacrylate.

In certain embodiments, the invention relates to any one of the aforementioned methods, wherein the cross-linking agent is N,N'-methylenebisacrylamide.

In certain embodiments, the invention relates to any one of the aforementioned methods, wherein the covered support member is irradiated at about 350 nm.

In certain embodiments, the invention relates to any one of the aforementioned methods, wherein the period of time is about 1 minute, about 5 minutes, about 10 minutes, about 15 minutes, about 20 minutes, about 30 minutes, about 45 minutes, or about 1 hour.

In certain embodiments, the invention relates to any one of the aforementioned methods, wherein the composite material comprises macropores.

In certain embodiments, the invention relates to any one of the aforementioned methods, wherein the average pore diameter of the macropores is less than the average pore diameter of the pores.

EXEMPLIFICATION

The following examples are provided to illustrate the invention. It will be understood, however, that the specific details given in each example have been selected for purpose of illustration and are not to be construed as limiting the scope of the invention. Generally, the experiments were conducted under similar conditions unless noted.

Example 1

This example illustrates a method of preparing a cation-exchange material of the present invention with multi-modal functionality.

A 20 wt % solution was prepared by dissolving 2-carboxyethyl acrylate, 2-acrylamido-2-methyl-1-propanesulfonic acid, ethylene glycol phenyl ether methacrylate, 2-(methylthio) ethyl methacrylate in a molar ratio of 1:0.22:0.14:0.06, respectively, in a solvent mixture containing 27.0 wt % N,N'-dimethylacetamide, 61.0 wt % di(propylene glycol)dimethyl ether, 7.15 wt % 1,2-propanediol and 4.85 wt % water. Glycerol 1,3-diglycerolate diacrylate was used as a cross-linking agent to achieve cross-linking density of 8% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the following general procedure. A weighed support member was placed on a poly(ethylene) (PE) sheet and a monomer or polymer solution was applied the sample. The sample was subsequently covered with another PE sheet and a rubber roller was run over the sandwich to remove excess solution. In situ gel formation in the sample was induced by polymerization initiated by irradiation with the wavelength of 350 nm for the period of 10 minutes. The resulting composite material was thoroughly washed with RO and then placed in a solution containing 0.1 N sodium hydroxide and 0.1 N sodium chloride to transfer the membrane into $Na^+$-form. Thereafter membrane was washed with RO water and dried at room temperature.

Membranes were characterized in terms of solute flux, hIgG and lysozyme binding capacity, hIgG and lysozyme recovery.

Solute flux measurements through the composite materials were carried out after the samples had been wetted with RO water. As a standard procedure, a sample in the form of a disk of diameter 7.8 cm was mounted on a sintered grid of 3-5 mm thickness and assembled into a cell supplied with compressed nitrogen at a controlled pressure. The cell was filled with 85 mM sodium acetate buffer containing 250 mM NaCl, pH 4.5 and pressure of 100 kPa was applied. The buffer solution that passed through the composite material in a specified time was collected in a pre-weighed container and weighed. All experiments were carried out at room temperature and at atmospheric pressure at the permeate outlet. Each measurement was repeated three or more times to achieve a reproducibility of ±5%.

Protein adsorption experiments were carried out by the following procedure. In adsorption step, a composite material sample in a form of a single membrane disk of diameter 25 mm was installed into Natrix membrane holder. Waters 600E HPLC system was used for carrying out the membrane chromatographic studies. The cell and the membrane sample were primed by passing 85 mM sodium acetate buffer containing 250 mM sodium chloride, pH 4.5 and conductivity 30 mS/cm (buffer A). The UV absorbance (at 280 nm) of the effluent stream from the Natrix membrane holder and the system pressure were continuously recorded. Protein was dissolved in buffer A to prepare 0.5 mg/mL solution. Buffer A was referred as a binding buffer. The elution buffer, containing 25 mM TRIS/HCl, 250 mM NaCl, pH 8.2, was referred as buffer B. All buffers and protein solutions were filtered through a polyethersulfone (PES) microporous membrane with pore size of 0.2 μm (Nalgene).

In chromatographic experiments, buffer A was passed through the membrane until a stable UV absorbance baseline was established. The method developed for bind-elute experiment included following steps: in the first step the membrane was preconditioning with binding buffer A; in the second step, the protein dissolved in a buffer A passed through the membrane to reach 20-30% breakthrough; in the third step the membrane was washed with buffer A and in a final step protein was eluted from the membrane using a buffer B which passed through the membrane. Chromatographic experiments were performed at a flow rate of 1 mL/min.

Protein recovery was calculated as the amount of the desorbed substance compared to the amount of the substance applied to the membrane in the adsorption/binding step.

The composite material produced by this method had a solute flux of 2,950 kg/m²h at applied pressure of 100 kPa. Dynamic binding capacity at 10% breakthrough was 220.1 mg/mL for hIgG and 135.0 mg/mL for lysozyme. The recovery of hIgG and lysozyme exceeded 95%.

FIG. 1 shows the hIgG bind-elute curve obtained in described above experiment.

Example 2

This example illustrates a method of preparing a cation-exchange material of the present invention with multi-modal functionality A 23 wt % solution was prepared by dissolving 2-carboxyethyl acrylate, 2-acrylamido-2-methyl-1-propanesulfonic acid, ethylene glycol phenyl ether methacrylate, hydroxypropyl methacrylate in a molar ratio of 1:0.25:0.15:0.14, respectively, in a solvent mixture containing 26.3 wt % N,N'-dimethylacetamide, 59.6 wt % di(propylene glycol) dimethyl ether, 7.3 wt % 1,2-propanediol and 6.8 wt % water. Glycerol dimethacrylate (GDA) and 3-(acryloyloxy)-2-hydroxypropyl methacrylate (AHM) were used as cross-linking agents to achieve cross-linking density of 10.6% (mol/mol). Cross-linking agents GDA and AHM were added in a molar ratio of 1:0.9, respectively. The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO and then placed in a solution containing 0.1 N sodium hydroxide and 0.1 N sodium chloride to transfer the membrane into Na⁺-form. Thereafter membrane was washed with RO water and dried at room temperature.

Membrane thus obtained was characterized in terms of solute flux, hIgG binding capacity and hIgG recovery as described in Example 1.

The composite material produced by this method showed solute flux of 4,150.00 kg/m²h and hIgG binding capacity of 175.8 mg/mL at 10% breakthrough. The recovery of hIgG exceeded 95%.

Example 3

This example illustrates a method of preparing a cation-exchange material of the present invention with multi-modal functionality A 20.6 wt % solution was prepared by dissolving 2-carboxyethyl acrylate, 2-acrylamido-2-methyl-1-propanesulfonic acid, ethylene glycol phenyl ether methacrylate in a molar ratio of 1:0.26:0.15, respectively, in a solvent mixture containing 27.0 wt % N,N'-dimethylacetamide, 60.0 wt % di(propylene glycol)dimethyl ether, 6.5 wt % 1,2-propanediol and 6.5 wt % water. Glycerol propoxylate (1PO/OH) triacrylate was used as cross-linking agents to achieve cross-linking density of 7.7% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO and then placed in a solution containing 0.1 N sodium hydroxide and 0.1 N sodium chloride to transfer the membrane into Na⁺-form. Thereafter membrane was washed with RO water and dried at room temperature.

Membrane thus obtained was characterized in terms of solute flux, hIgG binding capacity and hIgG recovery as described in Example 1.

The composite material produced by this method showed solute flux of 2,740.00 kg/m²h and hIgG binding capacity of 144 mg/mL at 10% breakthrough. The recovery of hIgG exceeded 95%.

Example 4

This example illustrates effect of ionic strength on hIgG binding capacity of a cation-exchange material of the present invention with multi-modal functionality One of the most important features of mixed mode media is a salt tolerance. Due to dual functionality of mixed-mode media, containing hydrophobic and ionic elements, increasing ionic strength will disrupt ionic bonds but the increasing salt concentration will promote hydrophobic adsorption leading to the salt independent performance.

Figure 2:
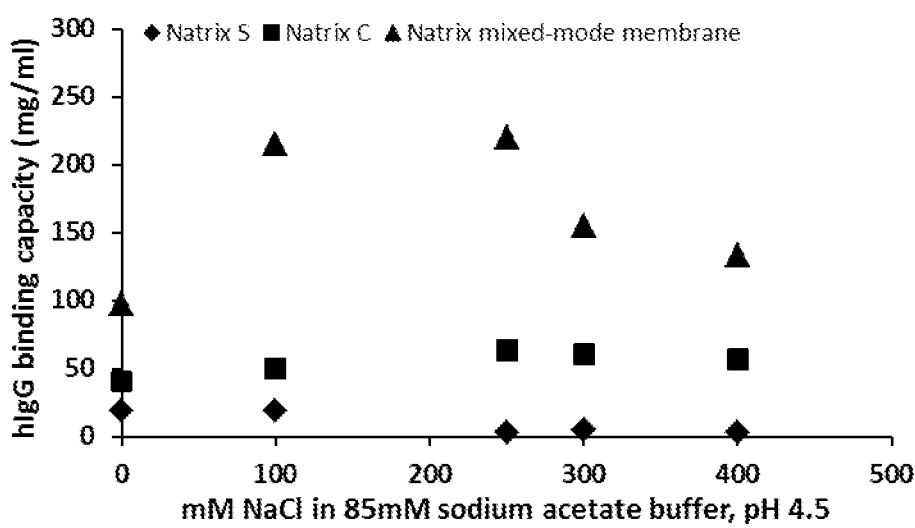
FIG. 2 depicts the performance of a mixed-mode membrane in a salt tolerance experiment investigating the effect of salt content in binding buffer on hIgG binding capacity.

Multimodal cation-exchange membrane prepared as described in Example 1 was used to examine an effect of ionic strength on hIgG binding capacity. 85 mM sodium acetate buffer containing sodium chloride ranging from 0 to 400 mM, pH 4.5 was used as a binding buffer. hIgG was dissolved in binding buffer with various ionic strength to prepare 0.5 mg/mL solution. Binding experiments were performed as described in Example 1. FIG. 2 illustrates hIgG dynamic binding capacity at 10% breakthrough as a function of salt content in a binding buffer. Natrix weak-cation exchange membrane (Natrix C) and Natrix strong cation exchange membrane (Natrix S) were also examined in the salt tolerance study (FIG. 2). As can be seen from FIG. 2, incorporating various functionalities in the mixed-mode membrane allows not only maintain salt-tolerance performance as also seen in the case of weak-cation exchange membrane (Natrix C), but enhance binding capacity as well. The multimodal membrane of the present invention can be successfully used in a much larger operating range in terms of conductivity of starting material than traditional cation exchangers. Secondly, mixed-mode membrane can be employed for direct load of clarified feed stocks, without prior dilution to reduce the conductivity of starting material.

Example 5

This example illustrates effect of pH on hIgG binding capacity of a cation-exchange material of the present invention with multi-modal functionality pH-dependent binding is one of the features of mixed-mode media. The later allows to use pH is an effective tool for protein elution without any change in conductivity of mobile phase. Because of the mixed-mode sorbents operate by a combination of hydrophobic and electrostatic interaction, mobile phase pH is greatly responsible for the shift from one type interaction to another.

Figure 3:
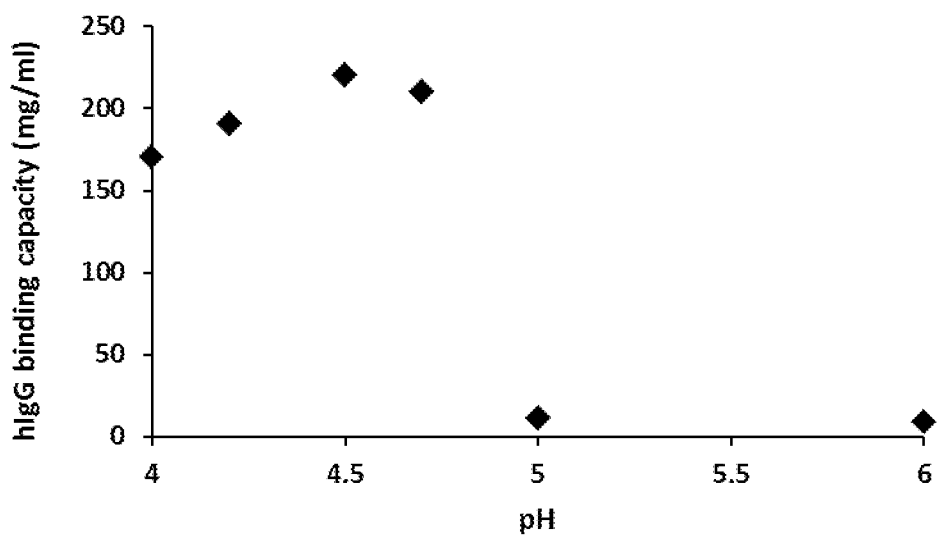
FIG. 3 depicts the performance of a mixed-mode membrane in an experiment investigating the effect of pH on hIgG binding capacity.

Multimodal cation-exchange membrane prepared as described in Example 1 was used to examine effect of pH on hIgG binding capacity. 85 mM sodium acetate buffer containing 250 mM sodium chloride was used as a binding buffer. pH was varied from 4.0 to 6.0. hIgG was dissolved in binding buffer with various pH to prepare 0.5 mg/mL solution. Binding experiments were performed as described in Example 1. FIG. 3 illustrates hIgG dynamic binding capacity at 10% breakthrough as a function of pH.

As pH is increased, binding capacity decreases, that consistent with fundamental mechanism.

Example 6

This example illustrates use of mixed-mode membrane in bind-elute mode to purify monoclonal antibodies Enhanced removal of antibody aggregates from a preparation or protein A purified monoclonal antibody can be successfully achieved by using mixed-mode media in bind-elute mode. "Bind-elute" mode is an operational approach to chromatography in which the buffer conditions are established so that both a target protein (e.g., non-aggregated antibody) and undesired contaminants (e.g., aggregated antibody) bind to the mixed mode chromatography support. Fractionation of intact non-aggregated protein is achieved subsequently by changing the conditions such that the target of interest is eluted from the support while contaminants remain bound. These contaminants may optimally be removed by an appropriate cleaning buffer.

Figure 4:
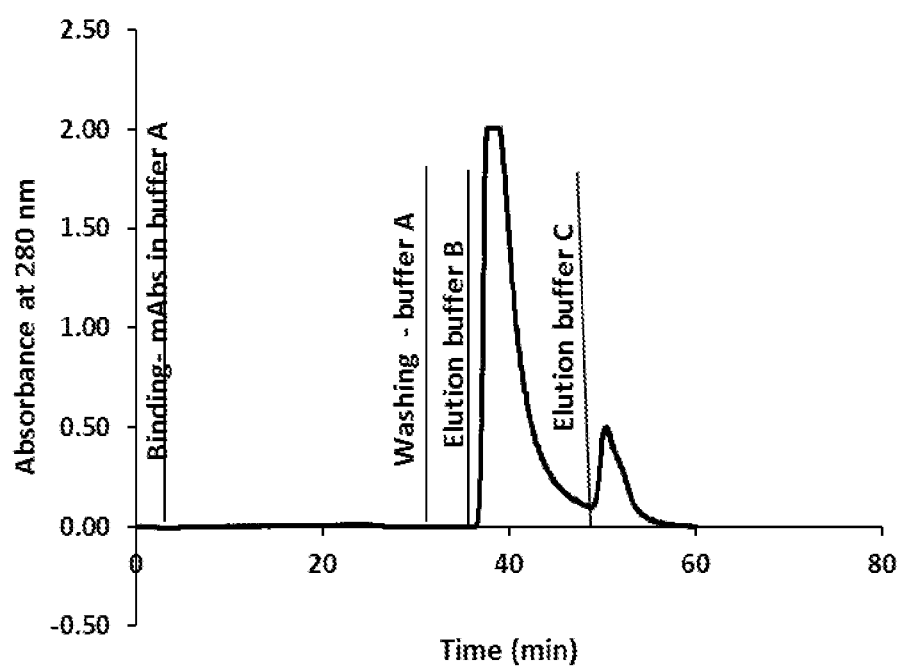
FIG. 4 depicts the performance of a mixed-mode membrane in bind-elute mode to purify monoclonal antibodies.

Multimodal cation-exchange membrane prepared as described in Example 1 was used to examine membrane performance in bind-elute mode to purify monoclonal antibodies. 85 mM sodium acetate buffer containing 250 mM sodium chloride, pH 4.5 was used as a binding buffer A. Protein A purified monoclonal antibody (mAbs) was dissolved in binding buffer A to prepare 0.5 mg/mL solution. Membrane was equilibrated at a flow rate of 1 mL/min with buffer A as described in Example 1. mAbs solution was applied to the membrane to achieve 80% of 10% breakthrough dynamic binding capacity, washed with equilibration buffer A, and then eluted in two steps. First step included the use of 100 mM MES buffer containing 135 mM NaCl, pH 5.7 as elution buffer B while 25 mM TRIS/HCl buffer containing 250 mM NaCl, pH 8.2 was used in a second step as elution buffer C (FIG. 4). Eluents were analyzed on SEC column TSKgel G3000SW$_{xl}$ (Tosoh Bioscience). 100 mM sodium phosphate buffer containing 100 mM sodium sulphate, pH 6.7 was used as a mobile phase. 800 µL sample was applied into the column at 0.80 mL/min.

Figure 5:
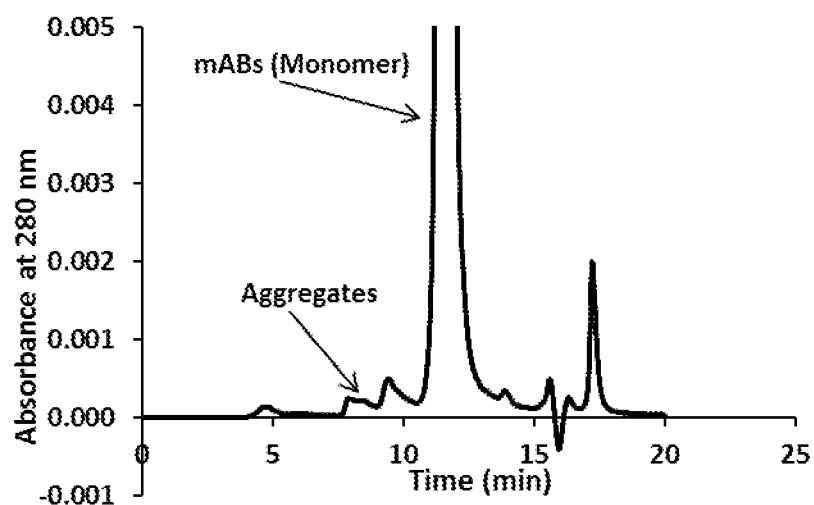
FIG. 5 depicts SEC column analysis: mAbs feed solution.

FIG. 4 presents performance of mixed-mode membrane in bind-elute mode. Two-step elution allows separating non-aggregated mAbs from aggregates (FIG. 5-7).

Figure 6:
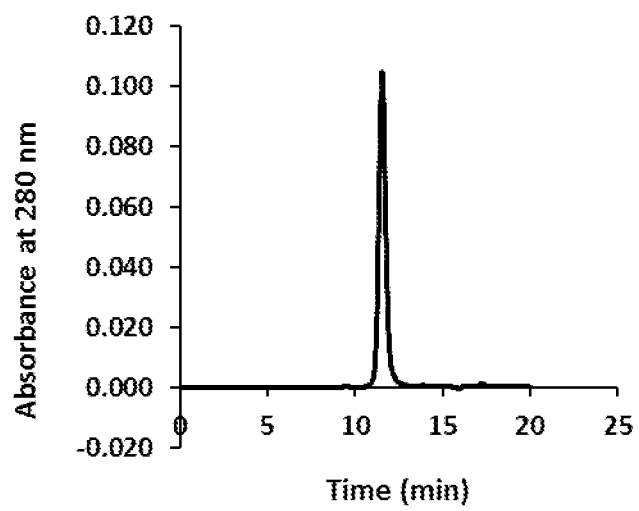
FIG. 6 depicts SEC column analysis: purification of mAbs post protein using mixed-mode membrane in bind-elute mode-eluent B.
Figures 7, 8, 9:
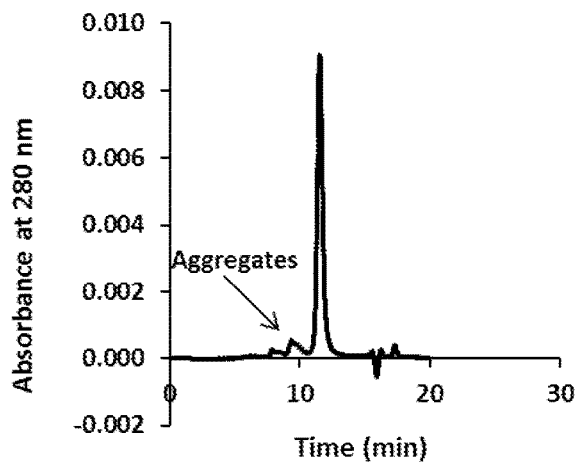
FIG. 7 depicts SEC column analysis: purification of mAbs post protein A using mixed-mode membrane in bind-elute mode-eluent C.
FIG. 8 tabulates performance results for multicycle mixed-mode membranes.
FIG. 9 tabulates the dynamic binding capacity at 10% breakthrough for various mixed-mode media.

As can be seen from FIG. 6 first fraction of mAbs eluted with buffer B contain significantly lower amount of aggregates compare to the feed solution. This mixed-mode membrane selectively reduced amount of aggregates from 1.51% to 0.11% or by 93%. Second fraction of mAbs eluted with buffer C showed a significant amount of aggregates (FIG. 7).

Example 7

This example illustrates multicycles use of mixed-mode membrane in bind-elute mode.

Multimodal cation-exchange membrane prepared as described in Example 1 was used to examine membrane performance in multicycles. Bind-elute experiments were run as described in Example 1. Membrane was equilibrated with 100 mM sodium citrate buffer, pH 4.5, conductivity ~21.9 mS/cm. The same buffer was used as a binding buffer A. Protein A purified monoclonal antibody (mAbs) was dissolved in binding buffer to prepare 0.5 mg/mL solution. mAbs solution was applied to the membrane to achieve 20% breakthrough dynamic binding capacity, washed with equilibration buffer A, then eluted in two steps as described in Example 6. First step included the use of 100 mM MES buffer containing 135 mM NaCl, pH 5.7 as elution buffer B while 25 mM TRIS/HCl buffer containing 250 mM NaCl was used in a second step as elution buffer C. mAbs feed solution and eluents were analyzed on SEC column TSKgel G3000SW$_{xl}$ (Tosoh Bioscience). 100 mM sodium phosphate buffer containing 100 mM sodium sulphate, pH 6.7 was used as a mobile phase. 800 µL sample was applied into the column at 0.80 mL/min.

The effluent was monitored for UV absorbance at 280 nm to characterize the binding capacity of the membrane. The membrane was then cleaned with 0.1 M NaCl/0.1 M NaCl and equilibrated with buffer A for the second run. The run was repeated as described above. The membrane was then cleaned with 0.1 M NaCl/0.1 M NaCl and equilibrated with buffer A for the third run as described above. The run was repeated as described above. FIG. 8 presents performance of a multimodal membrane in multiple cycles.

SEC column analysis showed 1.5% aggregates in mAbs feed solution.

As can be seen from FIG. 8, Natrix multimodal membrane showed identical performance in three runs in terms of dynamic binding capacity and selective aggregates removal. Aggregates concentration in mAbs post protein A was reduced from 1.51% to 0.11% or by 93%.

Example 8

This example illustrates a method of preparing an anion-exchange material of the present invention with multi-modal functionality A multimodal strong anion-exchange media has a great potential to be used in post-protein A purification of monoclonal antibodies (mAbs) at process scale. The goal is to remove key contaminants such is DNA, host cell proteins (HCP), leached protein A, aggregates and viruses in a single step.

A 12.6 wt % solution was prepared by dissolving (ar-vinylbenzyl)trimethylammonium chloride as a monomer and trimethylolpropane triacrylate (TRIM-A) as a cross-linker in a solvent mixture containing 52.0 wt % 1,2-propanediol and 48.0 wt % di(propylene glycol) methyl ether acetate. Cross-linking agent TRIM-A was added to achieve cross-linking density of 13% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO and dried at room temperature.

Membrane thus obtained was characterized in terms of water, solute flux (100 mM sodium phosphate buffer, containing 150 mM sodium chloride, pH 7.0) and protein A binding capacity as described Example 1. Protein A was dissolved in 100 mM sodium phosphate buffer containing 150 mM sodium chloride, pH 7.0

The composite material produced by this method showed water flux of 1,850.00 kg/m$^2$h at 100 kPa, solute flux of 2,270.00 kg/m$^2$h and protein A binding capacity of 85.8 mg/mL at 10% breakthrough.

Example 9

This example illustrates use of mixed-mode membrane in flow-through mode to purify monoclonal antibodies Removal antibody aggregates from a preparation or protein A purified monoclonal antibody can be successfully achieved by using mixed-mode media in a flow-through mode. The later refers to an operational approach to chromatography in which the buffer conditions are established so that intact non-aggregated protein to be purified flows through the mixed mode chromatography support upon application, while aggregates and other large molecules (including viruses) are selectively retained, thus achieving their removal.

Multimodal anion-exchange membrane prepared as described in Example 8 was used to examine membrane performance in flow-through mode to purify monoclonal antibodies. Membrane was equilibrated at a flow rate of 1 mL/min with 100 mM sodium phosphate buffer containing 250 mM sodium chloride (buffer A) as described in Example 1. Protein A purified monoclonal antibody (mAbs) was dissolved in buffer A and 300 mg mAbs/mL was applied to the membrane at flow rate of 1 mg/mL. mAbs feed and flowthrough fraction were analyzed on SEC column TSKgel G3000SW$_{xl}$ (Tosoh Bioscience). 100 mM sodium phosphate buffer containing 100 mM sodium sulphate, pH 6.7 was used as a mobile phase. 800 µL sample was applied into the column at 0.80 mL/min. The aggregate level was reduced from 1.51% to 0.32%.

Example 10

This example illustrates a method of preparing a anion-exchange material of the present invention with multi-modal functionality A 25 wt % solution was prepared by dissolving 2-(diethylamino)ethyl methacrylate, (ar-vinylbenzyl)trimethylammonium chloride, ethylene glycol phenyl ether methacrylate and 2-aminoethyl methacrylate in a molar ratio of 1:0.36:0.52:0.1, respectively, in a solvent mixture containing 72.5 wt % 1,3-Butanediol and 27.5 wt % N,N'-dimethylacetamide. Ethylene glycol dimethacrylate was used as cross-linking agent to achieve cross-linking density of 12.2% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO and dried at room temperature.

Membrane thus obtained was characterized in terms of water, solute flux (100 mM sodium phosphate buffer, containing 250 mM sodium chloride, pH 7.0) as described in Example 1 and aggregates removal from monoclonal antibodies in flow-through mode as described in Example 9. Protein A purified monoclonal antibody (mAbs) was dissolved in buffer A and 400 mg/mL was applied to the membrane at flow rate of 1 mg/mL. mAbs feed and flowthrough fraction were analyzed on SEC column TSKgel G3000SW$_{xl}$ (Tosoh Bioscience). 100 mM sodium phosphate buffer containing 100 mM sodium sulphate, pH 6.7 was used as a mobile phase. 800 µL sample was applied into the column at 0.80 mL/min.

The composite material produced by this method showed water flux of 3,750.00 kg/m$^2$h and solute flux of 4,050.00 kg/m$^2$h. The aggregate level was reduced from 1.51% to 0.47%.

Example 11

This example illustrates a method of preparing a cation-exchange material of the present invention with multi-modal functionality A 19.3 wt % solution was prepared by dissolving 2-carboxyethyl acrylate, 2-acrylamido-2-methyl-1-propanesulfonic acid, 2-(methylthio)ethyl methacrylate, 2-aminoethyl methacrylate hydrochloride and ethylene glycol phenyl ether methacrylate in a molar ratio of 1:0.34:0.05:0.05:0.22, respectively, in a solvent mixture containing 26.7 wt % N,N'-dimethylacetamide, 61.5 wt % di(propylene glycol) dimethyl ether, 7.1 wt % 1,2-propanediol and 4.7 wt % water. N,N'-methylenebisacrylamide was used as cross-linking agents to achieve cross-linking density of 5.4% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO and then placed in a solution containing 0.1 N sodium hydroxide and 0.1 N sodium chloride to transfer the membrane into Na$^+$-form. Thereafter membrane was washed with RO water and dried at room temperature.

Membrane thus obtained was characterized in terms of solute flux (85 mM sodium acetate buffer/250 mM NaCl, pH 4.5), hIgG binding capacity and hIgG recovery as described in Example 1.

The composite material produced by this method showed solute flux of 2,744.00 kg/m$^2$h and hIgG binding capacity of 181 mg/mL at 10% breakthrough. The recovery of hIgG exceeded 95%.

Example 12

This example illustrates selectivity of a cation-exchange material of the present invention with multi-modal functionality Selectivity is the most important factor in a separation. Mixed-mode media combines both ion-exchange and hydrophobic characteristics so that its selectivity can be manipulated in order for the retention magnitude of each retention mode to be adjusted by changing mobile phase ionic strength, pH and the organic solvent content, either individually or concurrently.

Figure 10:
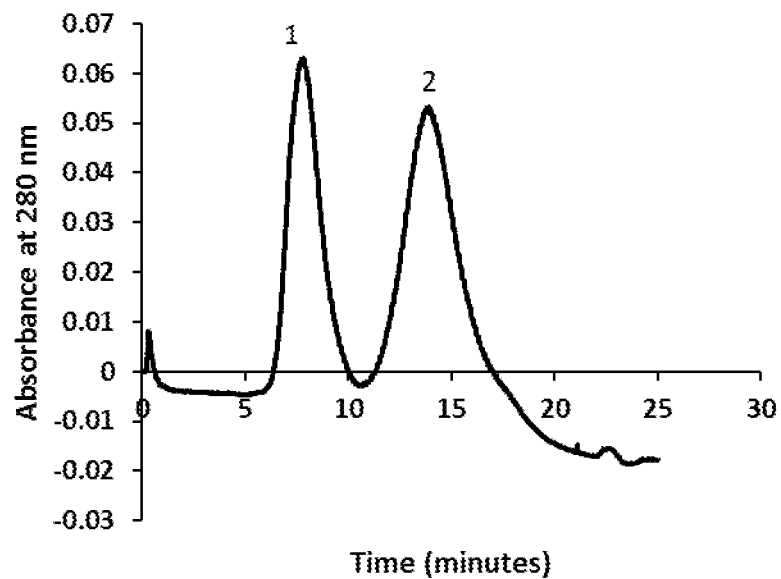
FIG. 10 depicts selective separation of Cytochrome C (1) and lysozyme (2) onto mixed-mode membrane prepared according to the Example 11.

Mixed-mode membrane prepared in Example 11 was used in selectivity study. Membrane was tested using a single layer inserted into a stainless steel disk holder attached to typical HPLC equipment. Chromatographic study on selective separation of lysozyme and cytochrome C was carried out using 20 mM sodium phosphate buffer, pH 6.5 as the mobile phase (Buffer A). Linear gradient elution was performed from buffer A to buffer B, using 20 mM sodium phosphate buffer containing 1.0 M sodium chloride as elution buffer B. Waters 600E HPLC system was used for carrying out the membrane chromatographic study. A 100 μL loop was used for injecting a 50 μL sample of protein mixture (5 mg/mL lysozyme and 3 mg/mL Cytochrome C). The UV absorbance (at 280 nm) of the effluent stream from the membrane holder and the system pressure were continuously recorded. The flow rate was 2 mL/min. All chromatographic studies were performed at 25° C. FIG. 10 shows selective separation of proteins on mixed-mode membrane of the present invention.

Example 13

This example illustrates caustic stability of a cation-exchange material of the present invention with multi-modal functionality Sodium hydroxide is widely accepted for cleaning, sanitizing and storing chromatography media and systems. The benefits of its use include efficacy, low cost, ease of detection, removal and disposal Sodium hydroxide has been shown to be effective in removing proteins and nucleic acids. It is also effective for inactivating most viruses, bacteria, yeasts, and endotoxins In order to maintain selectivity and binding capacity, chromatography media and systems have to be cleaned and are typically cleaned under alkaline conditions, e.g., with sodium hydroxide. For example, a standard process which is used for cleaning and restoring the media is a cleaning-in-place (CIP) alkaline protocol, which typically involves treatment of the membranes with 0.5 M NaOH. Thus, membranes developed for chromatography applications MUST be able to withstand conventional alkaline cleaning for a prolonged period of time.

Figure 11:
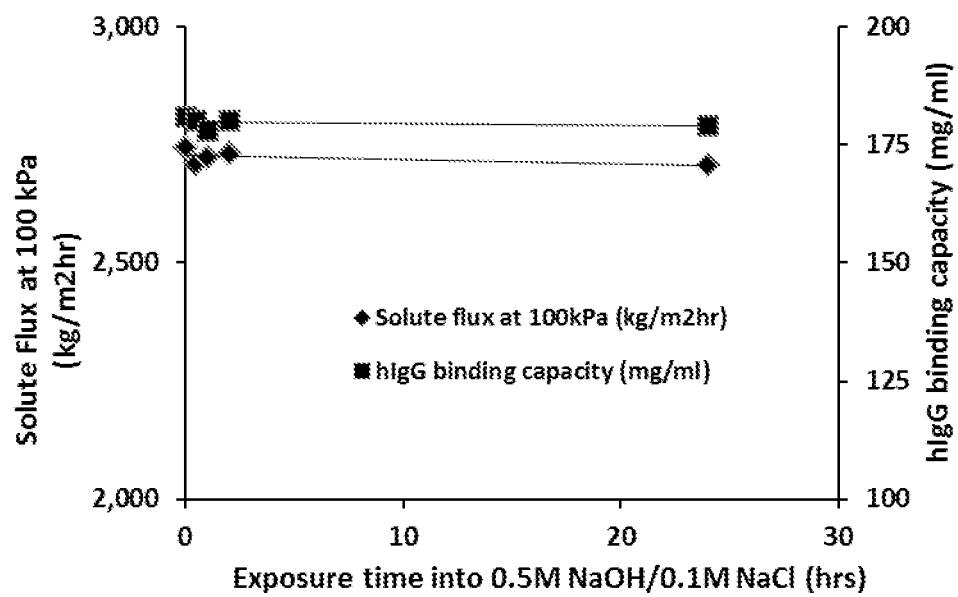
FIG. 11 depicts the effect of membrane exposure into 0.5 M NaOH/0.1 M NaCl on membrane performance.

A multimodal cation-exchange membrane prepared as described in Example 11 was used to examine an effect of membrane exposure into 0.5 M sodium hydroxide on its performance. Membrane was placed into 0.5 M sodium hydroxide containing 0.1 M NaCl for period of time ranging from 30 min to 24 hrs. Thereafter, the membrane was washed with RO water and equilibrated with 85 mM sodium acetate buffer containing 250 mM sodium chloride, pH 4.5. Then, solute flux and hIgG binding capacity were measured as described in Example 1. FIG. 11 illustrates effect of membrane exposure into 0.5 M sodium hydroxide containing 0.1 M sodium chloride onto its solute flux and hIgG binding capacity.

As can be seen from FIG. 11, membrane showed great caustic stability. No significant changes in membrane performance after exposure into 0.5 M NaOH/0.1 M NaCl for up to 24 hrs were observed.

Example 14

This example illustrates use of mixed-mode membrane in bind-elute mode to purify monoclonal antibodies Multimodal cation-exchange membrane prepared as described in Example 11 was used to illustrate the use of mixed-mode membrane in bind-elute mode to purify monoclonal antibodies.

The membrane chromatographic experiments were carried out using an AKTA™ Purifier liquid chromatographic system (GE Life Sciences). The UV absorbance, pH and conductivity of the effluent stream from the membrane holder and the system pressure were continuously monitored. The feed solution was prepared by spiking of 1 mg/mL Protein A purified monoclonal antibodies (mAbs) with 5.2 μg/mL host cell protein (HCP) and 100 μg/mL herring sperm DNA dissolved in 85 mM sodium acetate buffer containing 250 mM sodium chloride, pH 4.5 (Buffer A). The feed was loaded using a sample pump. Before injecting the feed solution into the membrane holder, the buffer A was passed through the membrane till stable readings were obtained. A target mAbs were eluted in two steps. In a first step 30 mM sodium phosphate buffer containing 15 mM sodium chloride, pH 6.5 was used as elution buffer (Buffer B) and in the second step 25 mM TRIS/HCl buffer containing 1.0 M sodium chloride was used as elution buffer (buffer C). Eluent from the first elution step (buffer B) was collected in 8 fractions (A1-A8). HCP levels and DNA concentrations were measured in combined fractions (A1-A5) and (A6-A8) and in the feed fraction.

HCP levels were determined with a broadly reactive Chinese Hamster Ovary (CHO) HCP ELISA kit (Cygnus Technologies F550). Calibration was performed with the HCP used in the chromatographic experiments. Calibrators and samples were diluted with Sample Diluent (Cygnus 1028). Measurements were performed on a Thermo Scientific Multiskan Ascent® Plate Reader.

DNA concentrations were measured with a DNA Assay (Life Technologies Quant-iT™ PicoGreen® dsDNA Assay Kit P11496). λ DNA standard and samples were diluted with 85 mM sodium acetate buffer containing 250 mM sodium chloride, pH 4.5. Measurements were performed on a Thermo Scientific Fluoroskan Ascent® Plate Reader.

Samples from feed solution and flowthrough fraction were also analyzed using absorption spectrophotometry. Absorption measurements were taken at wavelengths of 260 and 280 nanometers (nm). $A_{260}/A_{280}$ absorption ratios were computed from the measurements. An $A_{260}/A_{280}$ of a greater than equal to 1.8 was interpreted to indicate the sample analyzed therein was relatively free of protein.

mAbs feed and elution fractions A6-A8 were also analyzed on SEC column TSKgel G3000SW$_{xl}$ (Tosoh Bioscience) (FIG. 13). 100 mM sodium phosphate buffer containing 100 mM sodium sulphate, pH 6.7 was used as a mobile phase. 800 μL sample was applied into the column at 0.75 mL/min.

Figures 14, 15:
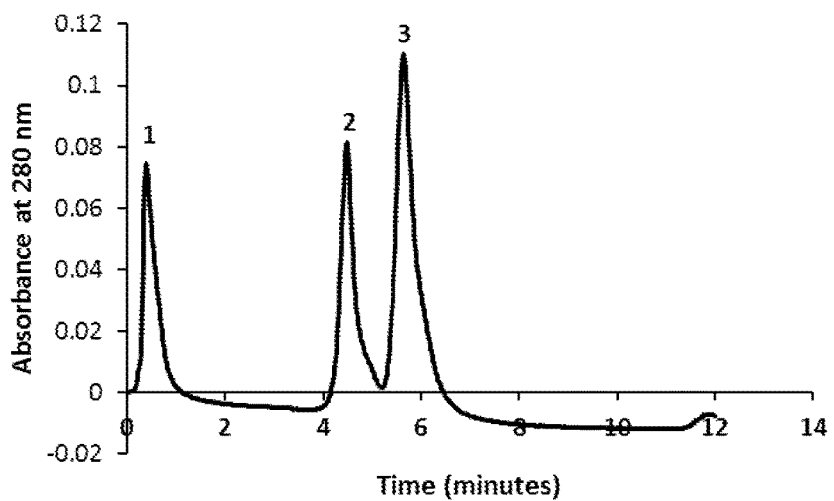
FIG. 14 depicts summary data on HCP/DNA clearance in elution fractions.
FIG. 15 depicts the selective separation of myoglobin (1), ribonuclease A (2) and lysozyme (3) onto mixed-mode membrane prepared according to the Example 17.

A summary of HCP/DNA clearance data is presented in FIG. 14.

Figures 12, 13:
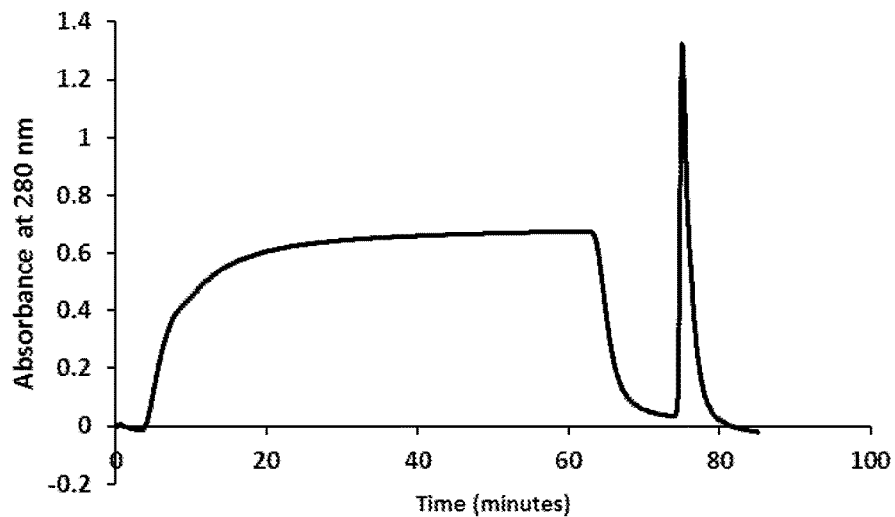
FIG. 12 depicts the removal of aggregates from hIgG using anion-exchange mixed-mode membrane.
FIG. 13 depicts summary data on aggregates clearance in elution fractions.

As can be seen from FIG. 13 and FIG. 14 mixed-mode membrane described in Example 11 showed the superior performance in terms of HCP/DNA clearance as well as aggregates clearance. The membrane can be used in a capture step in antibody processes.

Example 15

This example illustrates a method of preparing an anion-exchange material of the present invention with multi-modal functionality A 13.7 wt % solution was prepared by dissolving (ar-vinylbenzyl)trimethylammonium chloride, 2-aminoethyl methacrylate hydrochloride and ethylene glycol phenyl ether methacrylate in a molar ratio of 1:0.46:0.085, respectively, in a solvent mixture containing 52.7 wt % 1,2-propanediol, 41.9 wt % tri(propylene glycol) propyl ether and 5.4 wt % water. Trimethylolpropane trimethacrylate was used as cross-linking agents to achieve cross-linking density of 9.4% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO and dried at room temperature.

Membrane thus obtained was characterized in terms of water, solute flux (100 mM sodium phosphate buffer, containing 150 mM sodium chloride, pH 7.0), protein A and herring sperm DNA binding capacities as described Example 1. Protein A was dissolved in 100 mM sodium phosphate buffer containing 150 mM sodium chloride, pH 7.0 and herring sperm DNA in 20 mM sodium phosphate buffer containing 150 mM sodium chloride, pH 6.5.

The composite material produced by this method showed water flux of 3,735.00 kg/m$^2$ hr at 100 kPa, solute flux of 4,330.00 kg/m$^2$ hr and protein A binding capacity of 125.5 mg/mL and herring sperm DNA binding capacity of 20 mg/mL at 10% breakthrough.

Example 16

This example illustrates use of mixed-mode membrane in flow-through mode to purify hIgG.

Multimodal anion-exchange membrane prepared as described in Example 15 was used to examine membrane performance in flow-through mode to purify hIgG from aggregates. Membrane was equilibrated at a flow rate of 1 mL/min with 20 mM sodium phosphate buffer containing 150 mM sodium chloride (buffer A) as described in Example 1. hIgG was dissolved in buffer A and 300 mg hIgG/mL was applied to the membrane at flow rate of 1 mg/mL. Aggregates were eluted with 100 mM sodium acetate buffer, pH 4.2 (FIG. 12). hIgG feed and flowthrough fraction were analyzed on SEC column TSKgel G3000SW$_{xl}$ (Tosoh Bioscience). 100 mM sodium phosphate buffer containing 100 mM sodium sulphate, pH 6.7 was used as a mobile phase. 800 µL sample was applied into the column at 0.80 mL/min. The aggregate level was reduced from 15.1% to 8.3%.

Example 17

This example illustrates a method of preparing a strong cation-exchange material of the present invention with multi-modal functionality.

A 13.2 wt % solution was prepared by dissolving 2-acrylamido-2-methyl-1-propanesulfonic acid sodium salt, N-isopropyl acrylamide and N-phenylacrylamide in a molar ratio of 1:0.18:0.1, respectively, in a solvent mixture containing 17.8 wt % N,N'-dimethylacetamide, 54.1 wt % di(propylene glycol)dimethyl ether, 17.2 wt % 1,2-propanediol and 10.9 wt % water. N,N'-Hexamethylenebis(methacrylamide) was used as a cross-linking agent to achieve cross-linking density of 12% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO and dried at room temperature.

Membrane thus obtained was characterized in terms of solute flux (85 mM sodium acetate buffer/250 mM NaCl, pH 4.5), hIgG binding capacity (hIgG was dissolved in 85 mM sodium acetate buffer/NaCl, pH 4.5 and conductivity of 15 mS/cm) and hIgG recovery as described in Example 1.

The composite material produced by this method showed solute flux of 1,564.00 kg/m$^2$ hr and hIgG binding capacity of 91.5 mg/mL at 10% breakthrough. The recovery of hIgG exceeded 95%.

Example 18

This example illustrates selectivity of a cation-exchange material of the present invention with multi-modal functionality.

Mixed-mode membrane prepared in Example 17 was used in selectivity study. Membrane was tested using a single layer inserted into a stainless steel disk holder attached to typical HPLC equipment. Chromatographic study on selective separation of myoglobin, ribonuclease A and lysozyme was carried out using 20 mM sodium phosphate buffer, pH 6.5 as the mobile phase (Buffer A). Linear gradient elution was performed from buffer A to buffer B, using 20 mM sodium phosphate buffer containing 1.0 M sodium chloride as elution buffer B. Waters 600E HPLC system was used for carrying out the membrane chromatographic study. A 100-4 loop was used for injecting a 50-4 sample of protein mixture (5.4 mg/mL ribonuclease A, 3.3 mg/mL myoglobin and 7 mg/mL lysozyme in a volume ratio of 1:0.25:0.15). The UV absorbance (at 280 nm) of the effluent stream from the membrane holder and the system pressure were continuously recorded. The flow rate was 3 mL/min. All chromatographic studies were performed at 25° C. FIG. 15 shows selective separation of proteins on mixed-mode membrane of the present invention.

Example 19

This example illustrates effect of nature of co-monomer used on performance of a strong cation-exchange material of the present invention with multi-modal functionality.

A series of multimodal strong cation-exchange membranes were prepared as described in Example 17 using various co-monomers. Thus, a 13.2 wt % solution was prepared by dissolving 2-acrylamido-2-methyl-1-propanesulfonic acid sodium salt, N-isopropyl acrylamide (NIPAM) (or N-[tris(hydroxymethyl)methyl]acrylamide (THMAAm) or N-(3-methoxypropyl) acrylamide (MPAAm) or N,N'-dimethylacrylamide (DMAAm)) and N-phenylacrylamide in a molar ratio of 1:0.18:0.1, respectively, in a solvent mixture containing 17.8 wt % N,N'-dimethylacetamide, 54.1 wt % di(propylene glycol)dimethyl ether, 17.2 wt % 1,2-propanediol and 10.9 wt % water. N,N'-Hexamethylenebis (methacrylamide) was used as cross-linking agent to achieve cross-linking density of 12% (mol/mol). The photo-initiator Irgacure 2959 was added in the amount of 1 wt % with respect to the mass of the monomers.

A composite materials were prepared from the solution and the support TR0671 B50 (Hollingsworth & Vose) using the photoinitiated polymerization according to the general procedure described above (Example 1). The samples were irradiated for 10 min at 350 nm. The resulting composite materials were thoroughly washed with RO and dried at room temperature.

Membranes thus obtained were characterized in terms of flux (85 mM sodium acetate buffer/250 mM NaCl, pH 4.5 and 25 mM TRIS/HCl, 250 mM NaCl, pH 8.21), hIgG binding capacity and hIgG recovery as described in Example 1.

Figure 16:
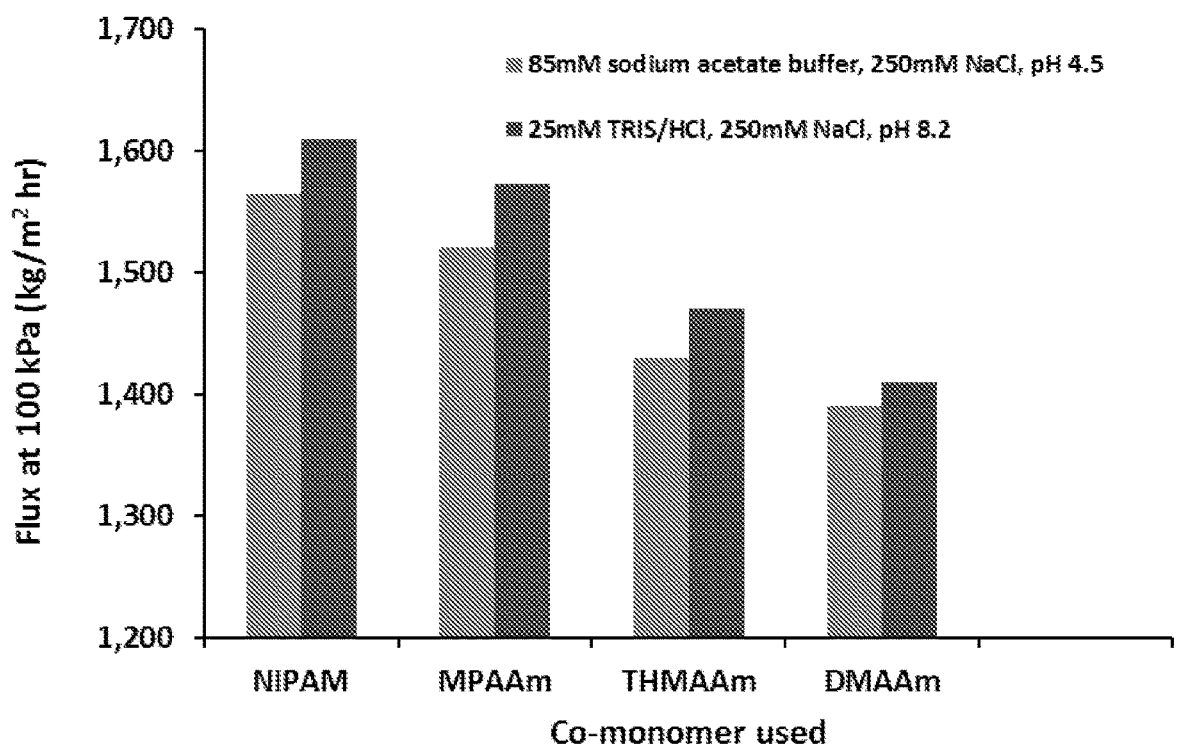
FIG. 16 depicts the effect of the nature of the co-monomer on membrane permeability.
Figure 17:
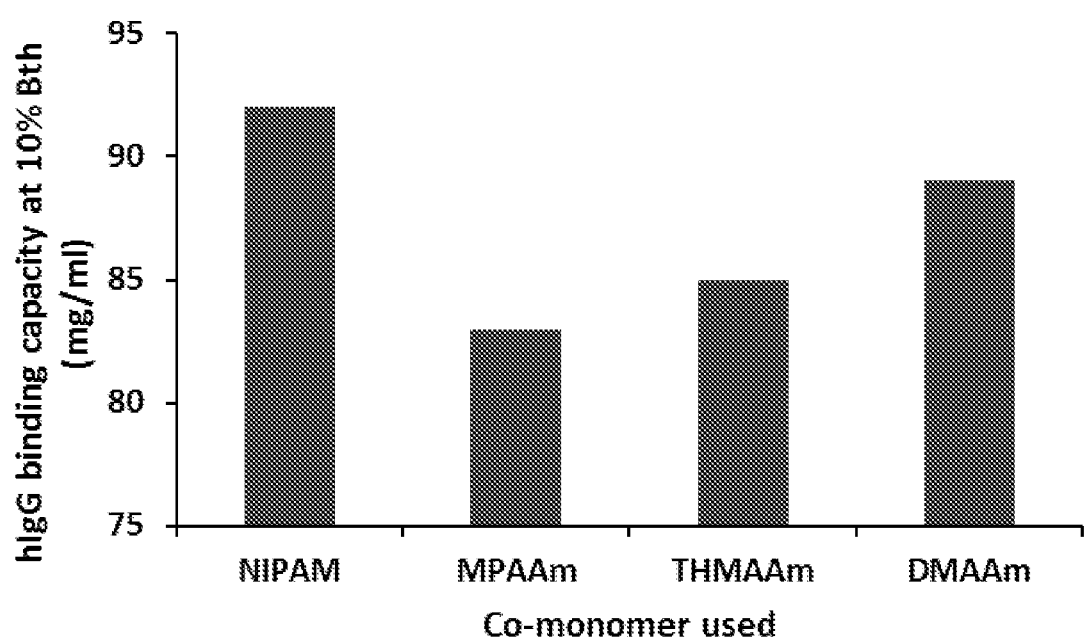
FIG. 17 depicts the effect of the nature of the co-monomer used on membrane performance.

FIGS. 16 and 17 illustrate effect of nature co-monomer used on membrane performance.

The recovery of hIgG exceeded 95% for all membranes examined.

Using N-isopropyl acrylamide as a co-monomer in the strong cation-exchange mixed-mode formulation resulted in the membrane with both good permeability characteristics and binding capacity.

Example 20

This example illustrates effect of nature of cross-linker used on performance of a strong cation-exchange material of the present invention with multi-modal functionality.

A series of multimodal strong cation-exchange membranes were prepared using various cross-linkers. Thus, A 14.5 wt % solution was prepared by dissolving 2-acrylamido-2-methyl-1-propanesulfonic acid sodium salt, N-isopropyl acrylamide and ethylene glycol phenyl ether methacrylate in a molar ratio of 1:0.1:0.15, respectively, in a solvent mixture containing 23.7 wt % N,N'-dimethylacetamide, 55.5 wt % tri(propylene glycol) methyl ether, 8.7 wt % 1,2-propanediol and 12.1 wt % water. N,N'-Methylenebisacrylamide (BIS) (or N,N'-hexamethylenebis(methacrylamide (Hexa-BIS) or 2,4,6-triallyloxy-1,3,5-triazine (T-XL-1) or 1,3,5-triallyl-1,3,5-triazine-2,4,6-(1H,3H,5H)-trione (T-XL-2) or 1,3,5-triacryloylhexahydro-1,3,5-triazine (T-XL-3) or glyoxal bis(diallylacetal) (GBDA or GBDE)) were used as cross-linkers to achieve cross-linking density of 10% (mol/mol). The photo-initiator Irgacure 2959 was added in the amount of 1 wt % with respect to the mass of the monomers.

A composite materials were prepared from the solution and the support TR0671 B50 (Hollingsworth & Vose) using the photoinitiated polymerization according to the general procedure described above (Example 1). The samples were irradiated for 10 min at 350 nm. The resulting composite materials were thoroughly washed with RO and dried at room temperature.

Membranes thus obtained were characterized in terms of flux (85 mM sodium acetate buffer/250 mM NaCl, pH 4.5 and 25 mM TRIS/HCl, 250 mM NaCl, pH 8.2), hIgG binding capacity and hIgG recovery as described in Example 1.

Figure 18:
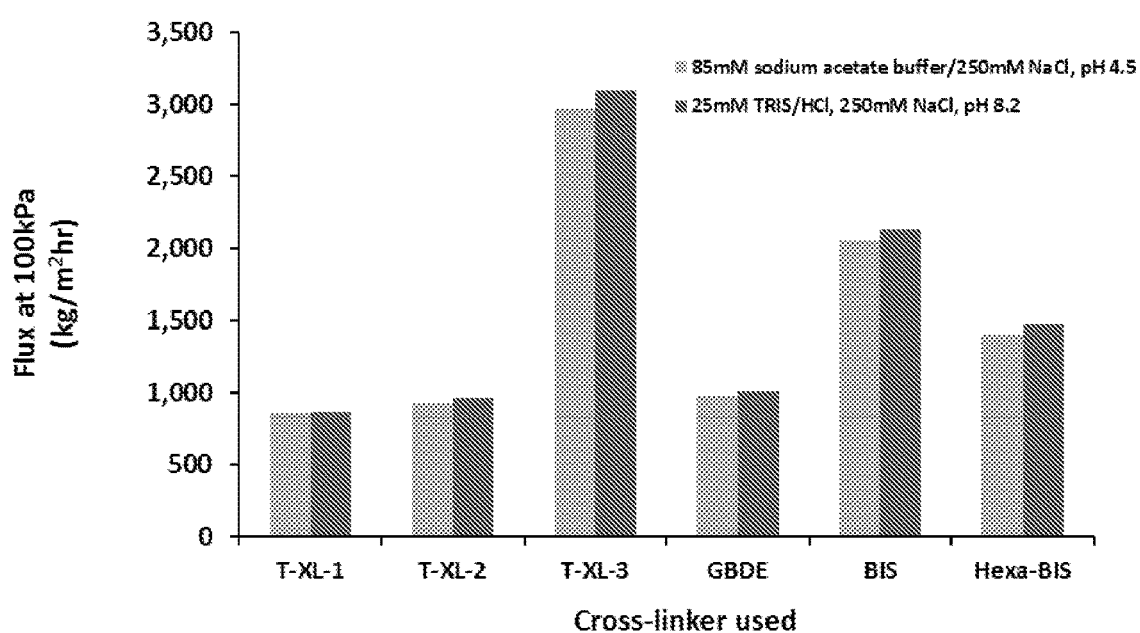
FIG. 18 depicts the effect of the nature of the cross-linker on membrane permeability.
Figure 19:
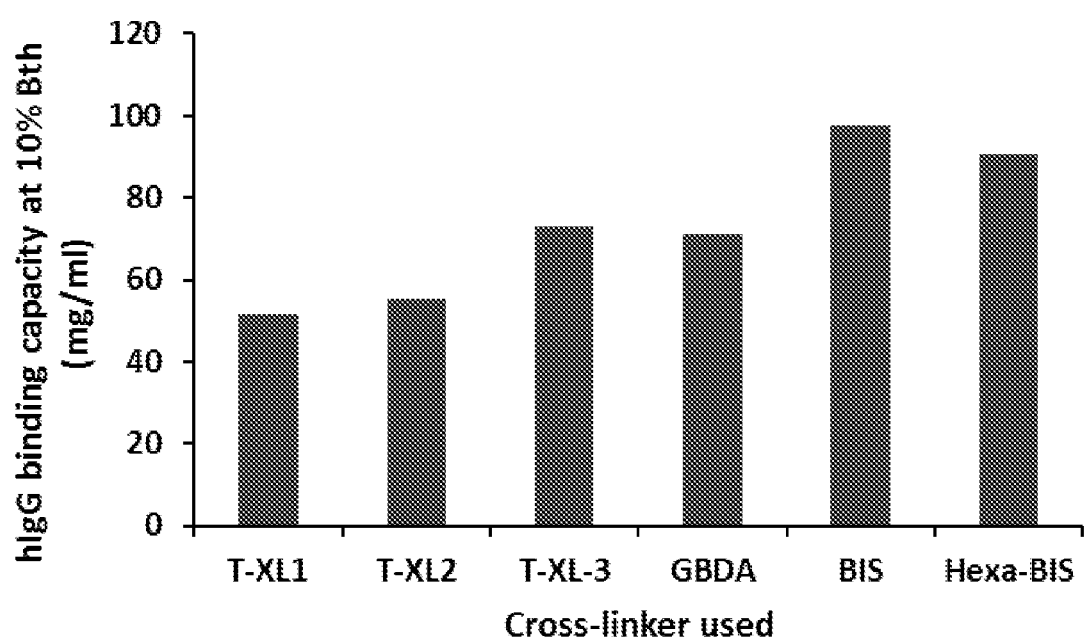
FIG. 19 depicts the effect of the nature of the cross-linker on membrane performance.

FIGS. 18 and 19 illustrate effect of nature cross-linker used on membrane performance.

The recovery of hIgG exceeded 95% for all membranes examined.

As can be seen from the data presented above, in FIG. 18 and FIG. 19, nature of cross-linking agent used plays a significant role in controlling the size of the membrane pores, the pore volume fraction and the interconnections. By employing trifunctional cross-linker 1,3,5-triacryloylhexahydro-1,3,5-triazine, membrane with good permeability characteristics was obtained.

Example 21

This example illustrates a gel morphology of the anion-exchange material of the present invention with multi-modal functionality prepared according to Example 8.

Figure 20:
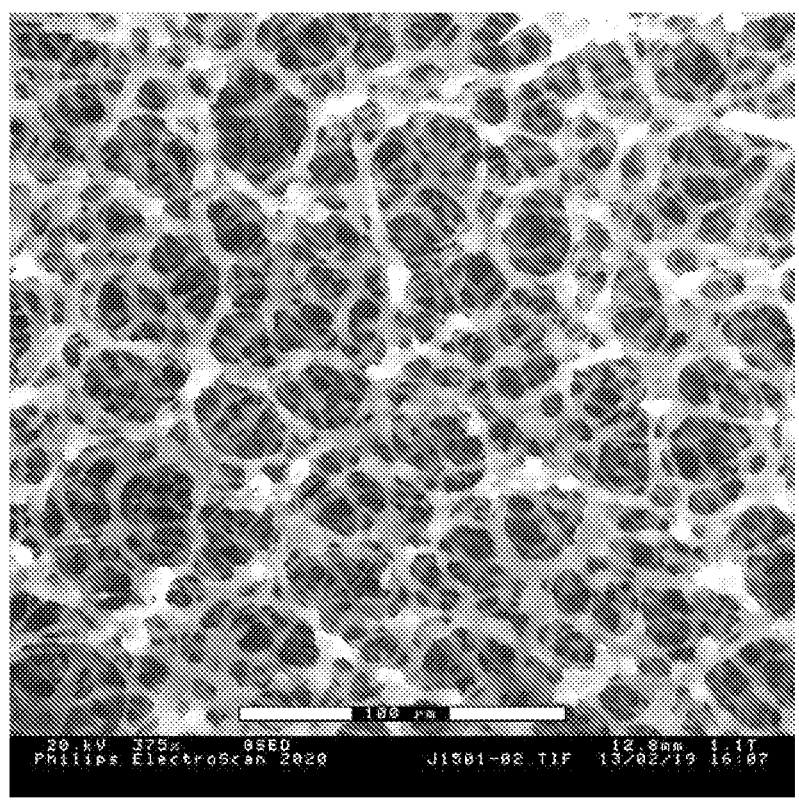
FIG. 20 depicts an ESEM micrograph of anion-exchange mixed-mode membrane prepared according to Example 8.

Gel morphology of mixed-mode membrane prepared according to Example 8 was examined with an environmental scanning electron microscope (ESEM, Philips Electroscan, model E-2020, Electroscan Corp., USA). A small sample of the membrane (3 mm×3 mm) was soaked in DI water, surface water was removed with wet filter paper and the wet membrane was placed in the sample chamber. An accelerating voltage of 20 kV was used in conjunction with a large spot size and magnifications less than 1500×, to limit both heating effects and sample damage. A working distance of 9-13 mm was employed to minimize the scattering of the beam. In the specimen chamber, the pressure was maintained between 1 and 4 Torr and the temperature was maintained at 3±0.5° C. using a Peltier-cooled sample stage. The sample chamber was periodically flushed with water vapor to maintain a satisfactory partial pressure of water, ensuring constant hydration of the membrane and preventing any drying of the sample that potentially can lead to some changes in membrane gel morphology. ESEM micrograph showed a developed macroporous structure of the anion-exchange mixed-mode membrane (FIG. 20).

Example 22

This example illustrates a gel morphology of the cation-exchange material of the present invention with multi-modal functionality prepared according to Example 11.

Figure 21:
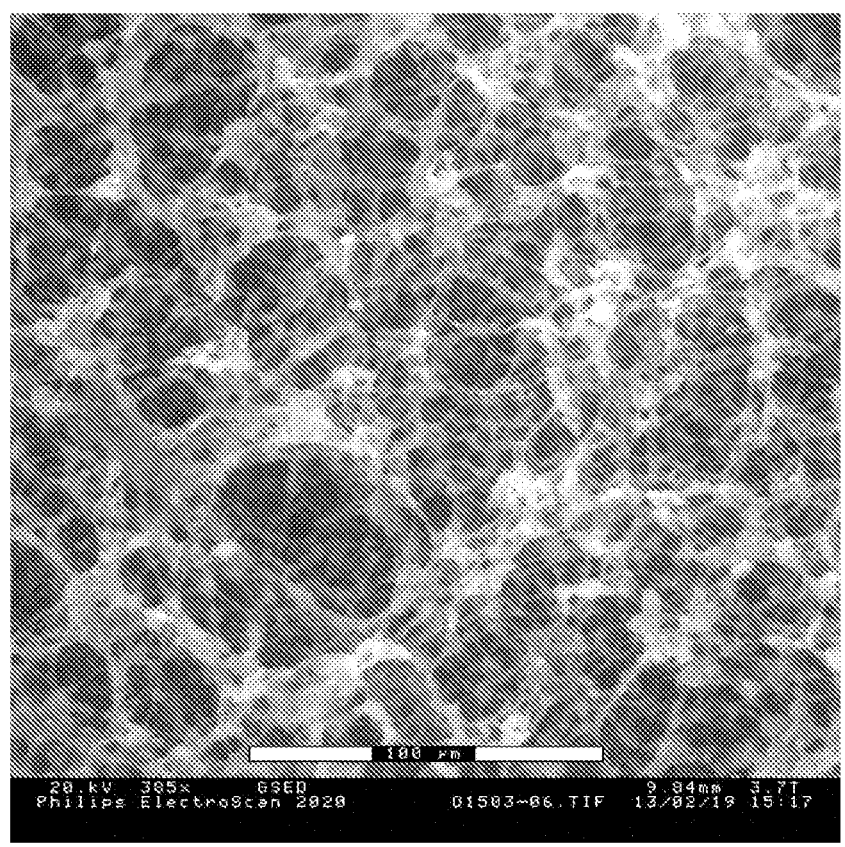
FIG. 21 depicts an ESEM micrograph of cation-exchange mixed-mode membrane prepared according to Example 11.

Gel morphology of mixed-mode membrane prepared according to Example 11 was examined using an environmental scanning electron microscope as described in Example 21 (FIG. 21).

As can be seen from FIG. 21, a cation-exchange mixed-mode membrane prepared according to Example 11 has a macroporous structure.

Example 23

This example illustrates a gel morphology of the cation-exchange material of the present invention with multi-modal functionality prepared according to Example 17.

Figure 22:
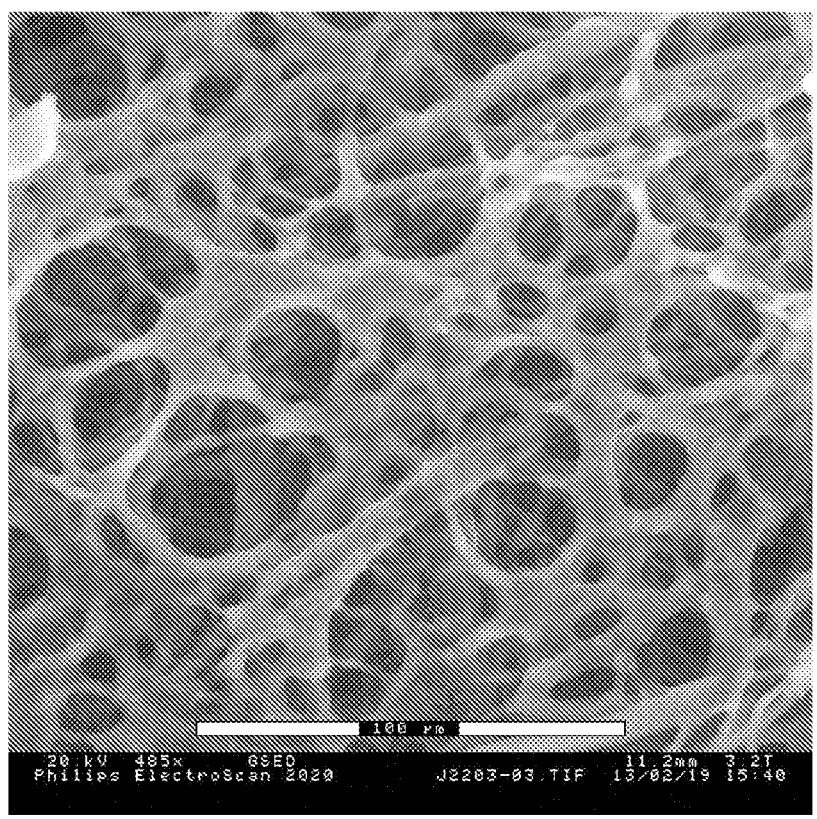
FIG. 22 depicts an ESEM micrograph of cation-exchange mixed-mode membrane prepared according to Example 17.

Gel morphology of mixed-mode membrane prepared according to Example 17 was examined using an environmental scanning electron microscope as described in Example 21 (FIG. 22).

As can be seen from FIG. 22, ESEM micrograph demonstrates a macroporous structure of a cation-exchange mixed-mode prepared according to Example 17.

Example 24

This example illustrates a method of preparing an anion-exchange material of the present invention with multi-modal functionality.

A 15.5 wt % solution was prepared by dissolving (3-acrylamido propyl) trimethylammonium chloride (75 wt % solution in water) and N-(3-N,N-dimethylaminopropyl) methacrylamide in a molar ratio of 1:1.17, respectively, in a solvent mixture containing 44.04 wt % N,N'-dimethylacetamide, 43.71 wt % di(propylene glycol) methyl ether acetate and 12.25 wt % water. N,N'-methylenebisacrylamide was used as cross-linking agent to achieve cross-linking density of 6.71% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO water at least three times.

Membrane thus obtained was characterized in terms of solute flux (25 mM Tris/HCl, pH 8.2) and BSA binding capacity using general procedure as described in Example 1.

The composite material produced by this method showed solute flux of 3,970.00 kg/m²h and BSA binding capacity of 87.4 mg/mL at 10% breakthrough using 25 mM Tris/HCl pH 8.2 as a binding buffer.

Pore size analysis of membrane was performed using a fully automated Capillary Flow Porometer—CFP-1500-AE (Porous Materials Inc., PMI). Membrane coupon (25 mm diameter) was cut from the sample. Excess water was removed with wetted filter paper and the average wet thickness was recorded using the micrometer. Thereafter, membrane coupon was placed on a support screen and installed on sample stage over airport in the CFP machine. Autotest was run according to a standard CFP procedure. The test showed mean flow pore diameter of 0.71 µm and bubble point pore diameter of 1.81 µm.

Example 25

This example illustrates a method of preparing an anion-exchange material of the present invention with multi-modal functionality.

A 13.6 wt % solution was prepared by dissolving (3-acrylamido propyl) trimethylammonium chloride (75 wt % solution in water), N-(3-N,N-dimethylaminopropyl) methacrylamide and N-tert-butyl acrylamide a molar ratio of 1:0.53:0.1, respectively, in a solvent mixture containing 60.32 wt % N,N'-dimethylacetamide, 29.01 wt % di(propylene glycol) methyl ether acetate and 10.67 wt % water. N,N'-methylenebisacrylamide was used as cross-linking agent to achieve cross-linking density of 9.91% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO at least three times.

Membrane thus obtained was characterized in terms of solute flux (25 mM Tris/HCl, pH 8.2) and BSA binding capacity using general procedure as described in Example 1.

The composite material produced by this method showed solute flux of 1,826.00 kg/m²h and BSA binding capacity of 151.5 mg/mL at 10% breakthrough using 25 mM Tris/HCl pH 8.2 as a binding buffer.

Pore size analysis of membrane was performed using a fully automated Capillary Flow Porometer—CFP-1500-AE (Porous Materials Inc.) as described in Example 24. The test showed mean flow pore diameter of 0.59 µm and bubble point pore diameter of 1.74 µm.

Example 26

This example illustrates a method of preparing an anion-exchange material of the present invention with multi-modal functionality.

A 11.8 wt % solution was prepared by dissolving (3-acrylamido propyl) trimethylammonium chloride (75 wt % solution in water) and N-tert-butyl acrylamide in a molar ratio of 1:0.09, respectively, in a solvent mixture containing 60.64 wt % N,N'-dimethylacetamide, 28.87 wt % di(propylene glycol) methyl ether acetate and 10.49 wt % water. N,N'-methylenebisacrylamide was used as cross-linking agent to achieve cross-linking density of 7.25% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO at least three times.

Membrane thus obtained was characterized in terms of solute flux (25 mM Tris/HCl, pH 8.2) and BSA binding capacity using general procedure as described in Example 1.

The composite material produced by this method showed solute flux of 1,235.00 kg/m²h and BSA binding capacity of 196.8 mg/mL at 10% breakthrough using 25 mM Tris/HCl pH 8.2 as a binding buffer.

Pore size analysis of membrane was performed using a fully automated Capillary Flow Porometer—CFP-1500-AE (Porous Materials Inc.) as described in Example 24. The test showed mean flow pore diameter of 0.31 µm and bubble point pore diameter of 1.50 µm.

Example 27

This example illustrates a method of preparing an anion-exchange material of the present invention with multi-modal functionality.

A 12.2 wt % solution was prepared by dissolving (3-acrylamido propyl) trimethylammonium chloride (75 wt % solution in water), N-tert-butyl acrylamide and diacetone acrylamide in a molar ratio of 1:0.1:0.1, respectively, in a solvent mixture containing 61.11 wt % N,N'-dimethylacetamide, 30.15 wt % di(propylene glycol) methyl ether acetate and 8.75 wt % water. N,N'-methylenebisacrylamide was used as cross-linking agent to achieve cross-linking density of 7.25% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO at least three times.

Membrane thus obtained was characterized in terms of solute flux (25 mM Tris/HCl, pH 8.2) and BSA binding capacity using general procedure as described in Example 1.

The composite material produced by this method showed solute flux of 1,075.00 kg/m²h and BSA binding capacity of 184.2 mg/mL at 10% breakthrough using 25 mM Tris/HCl pH 8.2 as a binding buffer.

Pore size analysis of membrane was performed using a fully automated Capillary Flow Porometer—CFP-1500-AE (Porous Materials, Inc.) as described in Example 24. The test showed mean flow pore diameter of 0.21 µm and bubble point pore diameter of 0.95 µm.

Example 28

This example illustrates a method of preparing an anion-exchange material of the present invention with multi-modal functionality.

A 12.8 wt % solution was prepared by dissolving (3-acrylamido propyl) trimethylammonium chloride (75 wt % solution in water), N-phenyl acrylamide and diacetone acrylamide in a molar ratio of 1:0.08:0.16, respectively, in a solvent mixture containing 61.89 wt % N,N'-dimethylacetamide, 29.97 wt % di(propylene glycol) methyl ether acetate and 8.14 wt % water. N,N'-methylenebisacrylamide was used as cross-linking agent to achieve cross-linking density of 10.43% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO at least three times.

Membrane thus obtained was characterized in terms of solute flux (25 mM Tris/HCl, pH 8.2) and BSA binding capacity using general procedure as described in Example 1.

The composite material produced by this method showed solute flux of 1,135.00 kg/m$^2$h and BSA binding capacity of 187.9 mg/mL at 10% breakthrough using 25 mM Tris/HCl pH 8.2 as a binding buffer.

Pore size analysis of membrane was performed using a fully automated Capillary Flow Porometer—CFP-1500-AE (Porous Materials Inc.) as described in Example 24. The test showed mean flow pore diameter of 0.29 μm and bubble point pore diameter of 1.15 μm.

Example 29

This example illustrates a method of preparing an anion-exchange material of the present invention with multi-modal functionality.

A 13.2 wt % solution was prepared by dissolving (3-acrylamido propyl) trimethylammonium chloride (75 wt % solution in water), N-(3-N,N-dimethylaminopropyl) methacrylamide and N-phenyl acrylamide in a molar ratio of 1:0.51:0.09, respectively, in a solvent mixture containing 62.18 wt % N,N'-dimethylacetamide, 29.55 wt % di (propylene glycol) methyl ether acetate and 11.33 wt % water. N,N'-methylenebisacrylamide was used as cross-linking agent to achieve cross-linking density of 10.43% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO at least three times.

Membrane thus obtained was characterized in terms of solute flux (25 mM Tris/HCl, pH 8.2) and BSA binding capacity using general procedure as described in Example 1.

The composite material produced by this method showed solute flux of 2,810.00 kg/m$^2$h and BSA binding capacity of 122.4 mg/mL at 10% breakthrough using 25 mM Tris/HCl pH 8.2 as a binding buffer.

Pore size analysis of membrane was performed using a fully automated Capillary Flow Porometer—CFP-1500-AE (Porous Materials Inc.) as described in Example 24. The test showed mean flow pore diameter of 0.65 μm and bubble point pore diameter of 1.69 μm.

Example 30

This example illustrates a method of preparing an anion-exchange material of the present invention with multi-modal functionality.

A 12.2 wt % solution was prepared by dissolving (3-acrylamido propyl) trimethylammonium chloride (75 wt % solution in water) and acrylic acid in a molar ratio of 1:1.19, respectively, in a solvent mixture containing 60.27 wt % N,N'-dimethylacetamide, 29.73 wt % di(propylene glycol) methyl ether acetate and 10.00 wt % water. N,N'-methylenebisacrylamide was used as cross-linking agent to achieve cross-linking density of 7.25% (mol/mol). The photo-initiator Irgacure 2959 was added in the amount of 1 wt % with respect to the mass of the monomers.

A composite material was prepared from the solution and the support TR0671 B50 (Hollingsworth & Vose) using the photoinitiated polymerization according to the general procedure described above (Example 1). The sample was irradiated for 10 min at 350 nm. The resulting composite material was thoroughly washed with RO at least three times.

Membrane thus obtained was characterized in terms of solute flux (25 mM Tris/HCl, pH 8.2) and BSA binding capacity using general procedure as described in Example 1.

The composite material produced by this method showed solute flux of 1,850.00 kg/m$^2$h and BSA binding capacity of 150.5 mg/mL at 10% breakthrough using 25 mM Tris/HCl pH 8.2 as a binding buffer.

Pore size analysis of membrane was performed using a fully automated Capillary Flow Porometer—CFP-1500-AE (Porous Materials Inc.) as described in Example 24. The test showed mean flow pore diameter of 0.57 μm and bubble point pore diameter of 1.44 μm.

Example 31

This example illustrates effect of hydrophobicity on membrane performance of cation-exchange material of the present invention with multi-modal functionality.

A 10.5 wt % solutions were prepared by dissolving 2-acrylamido-2-methyl-1-propane sulfonic acid (AMPS), N-phenyl acrylamide (PhAAm) or N-tert-butyl acrylamide (BuAAm) (PhAAm and BuAAm monomers are referred as Hm in FIG. 23 below) and N-hydroxyethyl acrylamide (HEAAm) in a solvent mixture containing N,N'-dimethylacetamide (DMAc), di(propylene glycol) methyl (DPM), di(propylene glycol) dimethyl ether (DMM), propylene carbonate (PrCarb), 1,2-propanediol (Prdiol) and water. N,N'-methylenebisacrylamide (BIS) was used as cross-linking agent. The photo-initiator Irgacure 2959 was added in the amount of 1 wt % with respect to the mass of the monomers. The formulations characteristics are presented in FIG. 23 below.

A composite materials were prepared from the solution and the support TR0671 B50 (Hollingsworth & Vose) using the photoinitiated polymerization according to the general procedure described above (Example 1). The samples were irradiated for 10 min at 350 nm. The resulting composite materials were placed into solution containing 0.25 M NaOH and 0.5 M NaCl for 10 min, and then membranes were thoroughly washed with RO at least three times and dried at room temperature.

Membranes thus obtained were characterized in terms of solute flux (85 mM NaAc/NaCl, conductivity 15 mS/cm, pH 4.4), hIgG binding capacity (BC) and protein recovery using general procedure as described in Example 1. A solution of 85 mM NaAc/NaCl, conductivity 15 mS/cm and pH 4.4 was used as a binding buffer and 25 mM Tris/HCl buffer containing 250 mM NaCl, pH 8.2 was used as elution buffer.

Swelling in water was measured as percentage increase in thickness after dry membrane was soaked in water for 15 min.

Pore size analysis of membrane was performed using a fully automated Capillary Flow Porometer—CFP-1500-AE (Porous Materials Inc.) as described in Example 24.

The performance characteristics of cation-exchange mixed-mode membranes with various hydrophobic components are presented in FIG. 24 below.

As can be seen from FIG. 24 phenyl-containing membrane showed lower buffer flux and higher dynamic binding capacity. The latter is consistent with more hydrophilic nature of the phenyl-based membrane compare with butyl-based membrane.

Example 32

This example illustrates an effect of co-monomers nature on performance of cation-exchange material of the present invention with multi-modal functionality.

A 10.5 wt % solutions were prepared by dissolving 2-acrylamido-2-methyl-1-propane sulfonic acid (AMPS), N-tert-butyl acrylamide (BuAAm) and N-isopropyl acrylamide (NIPAM) or N,N'-dimethyl acrylamide (DMAAm) or diacetone acrylamide (DAAm) or N-hydroxyethyl acrylamide (HEAAM) (co-monomers are referred as CM in FIG. 25 below) in a solvent mixture containing N,N'-dimethylacetamide (DMAc), di(propylene glycol) methyl (DPM), di(propylene glycol) dimethyl ether (DMM), propylene carbonate (PrCarb), 1,2-propanediol (Prdiol) and water. N,N'-methylenebisacrylamide (BIS) was used as cross-linking agent. The photo-initiator Irgacure 2959 was added in the amount of 1 wt % with respect to the mass of the monomers. The formulations characteristics are presented in FIG. 25 below.

Composite materials were prepared from the solution and the support TR0671 B50 (Hollingsworth & Vose) using the photoinitiated polymerization according to the general procedure described above (Example 1). The samples were irradiated for 4 min and 10 min at 350 nm. The resulting composite materials were placed into solution containing 0.25M NaOH and 0.5M NaCl for 10 min, and then membranes were thoroughly washed with RO at least three times and dried at room temperature.

Membranes irradiated for 10 min were characterized in terms of solute flux (85 mM NaAc/NaCl, conductivity 15 mS/cm, pH 4.4), hIgG binding capacity (BC) and protein recovery using general procedure as described in Example 1. A solution of 85 mM NaAc, conductivity of 15 mS/cm and pH 4.4 was used as a binding buffer and 25 mM Tris/HCl buffer containing 250 mM NaCl, pH 8.2 was used as elution buffer. Swelling in water was measured as percentage increase in thickness after dry membranes were soaked in water for 15 min.

Both membranes irradiated for 4 min and 10 min were characterized in terms of mean flow pore size and bubble point pore size. Pore size analysis of membranes was performed using a fully automated Capillary Flow Porometer—CFP-1500-AE (Porous Materials Inc.) as described in Example 24.

The performance characteristics of cation-exchange mixed-mode membranes with various hydrophobic components are presented in FIG. 26 below.

All selected co-monomers used in this Example are hydrophilic, completely/or partially water soluble and very compatible with AMPS-monomer in terms of polymerization rate. As it can be seen from FIG. 26, altering the type of comonomer results in membranes with varying buffer fluxes, hIgG dynamic binding capacity, pore size and swelling. NIPAM, DAAm and HEAAm-based membranes prepared at 4 min and 10 min polymerization time had similar mean flow pore size and bubble point pore size. The latter indicates high polymerization rate that occurred in these cases.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method, comprising the step of:
    contacting at a first flow rate a first fluid comprising a substance with a composite material, thereby adsorbing or absorbing a portion of the substance onto the composite material;
    contacting at a second flow rate a second fluid with the substance adsorbed or absorbed onto the composite material, thereby releasing a first portion of the substance from the composite material, and
    contacting at a third flow rate a third fluid with the substance adsorbed or absorbed onto the composite material, thereby releasing a second portion of the substance from the composite material:
wherein the composite material comprises:
    a support member, comprising a plurality of pores extending through the support member; and a cross-linked gel;
    wherein the cross-linked gel comprises a polymer derived from 2-acrylamido-2-methyl-1-propanesulfonic acid or a salt thereof, which comprises cation exchange functionality; a second monomer; and at least a third monomer;
    wherein the second monomer comprises hydrophobic functionality or pi-pi bond donating functionality and is selected from the group consisting of ethylene glycol phenyl ether methacrylate, N-phenyl acrylamide, and N-tert-butyl acrylamide;
    the third monomer is selected from the group consisting of 2-(methylthio)ethyl methacrylate, N-(3-methoxypropyl acrylamide), and diacetone acrylamide;
    the cross-linked gel is located in the pores of the support member; and
    the third fluid is different from the second fluid.

2. The method of claim 1, wherein the first fluid further comprises a fragmented antibody, aggregated antibodies, a host cell protein, a polynucleotide, an endotoxin, or a virus.

3. The method of claim 1, wherein the substance is a biological molecule or biological ion.

4. The method of claim 3, wherein the biological molecule or biological ion is selected from the group consisting of albumins, lysozyme, viruses, cells, y-globulins of human and animal origins, immunoglobulins of human and animal origins, proteins of recombinant and natural origins, polypeptides of synthetic and natural origins, interleukin-2 and its receptor, enzymes, monoclonal antibodies, trypsin and its inhibitor, cytochrome C, myoglobin, myoglobulin, a-chymotrypsinogen, recombinant human interleukin, recombinant fusion protein, nucleic acid derived products, DNA of synthetic and natural origins, and RNA of synthetic and natural origins.

5. The method of claim 1, wherein the first fluid is a clarified cell culture supernatant.

6. The method of claim 1, wherein the composite material is a membrane.

7. The method of claim 1, wherein the fluid flow path of the first fluid is substantially through the macropores of the composite material.

8. The method of claim 1, wherein the first fluid is a buffer.

9. The method of claim 1, wherein the pH of the first fluid is about 2, about 2.5, about 3, about 3.5, about 4, about 4.5, about 5, about 5.5, about 6, about 7, about 8, or about 9.

10. The method of claim 1, wherein the first fluid comprises a salt.

11. The method of claim 10, wherein the salt is selected from the group consisting of glycine-HCl, NaCl, and $NH_4Cl$.

12. The method of claim 1, wherein the concentration of the substance in the first fluid is about 0.2 mg/mL to about 10 mg/mL.

13. The method of claim 1, wherein the first flow rate is up to about 50 bed volumes/min.

14. The method of claim 1, wherein the fluid flow path of the second fluid is substantially through the macropores of the composite material.

15. The method of claim 1, wherein the second fluid is a buffer.

16. The method of claim 1, wherein the second fluid comprises a salt.

17. The method of claim 1, wherein the third fluid is a buffer.

18. The method of claim 1, wherein the third fluid comprises a salt.

19. The method of claim 1, wherein the cross-linked gel comprises a polymer derived from (a) 2-acrylamido-2-methyl-1-propanesulfonic acid, (b) the second monomer is N-tert-butyl acrylamide, and (c) the third monomer is diacetone acrylamide.

* * * * *